(12) United States Patent
Skakoon

(10) Patent No.: US 7,803,163 B2
(45) Date of Patent: Sep. 28, 2010

(54) MULTIPLE INSTRUMENT RETAINING ASSEMBLY AND METHODS THEREFOR

(75) Inventor: James G. Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1339 days.

(21) Appl. No.: 11/262,298

(22) Filed: Oct. 28, 2005

(65) Prior Publication Data

US 2006/0122629 A1    Jun. 8, 2006

Related U.S. Application Data

(63) Continuation-in-part of application No. 11/005,607, filed on Dec. 4, 2004, now Pat. No. 7,497,863.

(51) Int. Cl.
*A61B 19/00* (2006.01)
(52) U.S. Cl. ..................................... 606/130
(58) Field of Classification Search ................. 606/130; 248/68.1, 74.1
See application file for complete search history.

(56) References Cited

U.S. PATENT DOCUMENTS

| | | | |
|---|---|---|---|
| 431,187 A | 7/1890 | Foster | |
| 438,801 A | 10/1890 | Delehanty | |
| 873,009 A | 12/1907 | Baxter | |
| 1,129,333 A | 2/1915 | Clarke | |
| 1,664,210 A | 3/1928 | Hall | |
| 2,119,649 A | 6/1938 | Roosen | |
| 2,135,160 A | 11/1938 | Beekhuis | |
| 2,497,820 A * | 2/1950 | Kielland | ..................... 403/390 |
| 2,686,890 A | 8/1954 | Davis | |

(Continued)

FOREIGN PATENT DOCUMENTS

DE      3108766      9/1982

(Continued)

OTHER PUBLICATIONS

"Inomed Competence in Neurophysiologic Monitoring", http://www.inomed.com/english/index.htm,(observed Mar. 23, 2004), 2 pgs.

(Continued)

*Primary Examiner*—Julian W Woo
*Assistant Examiner*—Gregory Anderson
(74) *Attorney, Agent, or Firm*—Scott A. Marks; Harness, Dickey & Pierce, P.L.C.

(57) ABSTRACT

This patent document discusses, among other things, assemblies and methods for retaining a plurality of surgical instruments. In one example, a retaining assembly includes a floating seat having a seat first side and a seat second side. One or both of the seat first or second sides include at least one recessed portion to receive an instrument. In another example, a first clamp member is positioned adjacent the seat first side and a floating second clamp member is positioned adjacent the seat second side. An actuator engaged with an actuator receiving lumen is disposed adjacent the seat second side. Movement of the actuator in a first direction advances the first clamp member, the floating seat, and the floating second clamp member toward one another. In varying examples, the floating second clamp member comprises a rocker configured to pivot in three-dimensions, while the floating seat is configured to pivot in two-dimensions.

33 Claims, 16 Drawing Sheets

U.S. PATENT DOCUMENTS

| | | |
|---|---|---|
| 3,010,347 A | 11/1961 | Kron |
| 3,016,899 A | 1/1962 | Stenvall |
| 3,017,887 A | 1/1962 | Heyer |
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |
| 3,402,710 A | 9/1968 | Paleschuck |
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew et al. |
| 3,817,249 A | 6/1974 | Nicholson |
| 3,893,449 A | 7/1975 | Lee et al. |
| 3,981,079 A | 9/1976 | Lenczycki |
| 4,013,080 A | 3/1977 | Froning |
| 4,026,276 A | 5/1977 | Chubbuck |
| 4,040,427 A | 8/1977 | Winnie |
| 4,131,257 A * | 12/1978 | Sterling ................ 248/67.5 |
| 4,230,117 A | 10/1980 | Anichkov et al. |
| 4,265,252 A | 5/1981 | Chubbuck et al. |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen et al. |
| 4,618,978 A | 10/1986 | Cosman |
| 4,629,451 A | 12/1986 | Winters et al. |
| 4,638,798 A | 1/1987 | Shelden et al. |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,798,208 A | 1/1989 | Faasse, Jr. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist et al. |
| 5,116,345 A | 5/1992 | Jewell et al. |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson |
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,242,415 A | 9/1993 | Kantrowitz et al. |
| 5,246,448 A | 9/1993 | Chang |
| 5,257,998 A | 11/1993 | Ota et al. |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab et al. |
| 5,306,272 A | 4/1994 | Cohen et al. |
| 5,309,913 A | 5/1994 | Kormos et al. |
| 5,330,485 A | 7/1994 | Clayman et al. |
| 5,354,283 A | 10/1994 | Bark et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,394,457 A | 2/1995 | Leibinger et al. |
| 5,405,330 A | 4/1995 | Zunitch et al. |
| 5,423,832 A | 6/1995 | Gildenberg |
| 5,423,848 A | 6/1995 | Washizuka et al. |

| Patent | Date | Inventor |
|---|---|---|
| 5,445,166 A | 8/1995 | Taylor |
| 5,452,720 A | 9/1995 | Smith et al. |
| 5,464,446 A | 11/1995 | Dreessen et al. |
| 5,470,307 A | 11/1995 | Lindall |
| 5,474,564 A | 12/1995 | Clayman et al. |
| 5,483,961 A | 1/1996 | Kelly et al. |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. |
| 5,528,652 A | 6/1996 | Smith et al. |
| 5,541,377 A | 7/1996 | Stuhlmacher |
| 5,572,905 A | 11/1996 | Cook, Jr. |
| 5,572,999 A | 11/1996 | Funda et al. |
| 5,575,798 A | 11/1996 | Koutrouvelis |
| 5,618,288 A | 4/1997 | Calvo et al. |
| 5,622,170 A | 4/1997 | Schulz |
| 5,638,819 A | 6/1997 | Manwaring et al. |
| 5,639,276 A | 6/1997 | Weinstock et al. |
| 5,643,286 A | 7/1997 | Warner et al. |
| 5,647,361 A | 7/1997 | Damadian |
| 5,649,936 A * | 7/1997 | Real ............................ 606/130 |
| 5,658,272 A | 8/1997 | Hasson |
| 5,662,600 A | 9/1997 | Watson et al. |
| 5,667,514 A | 9/1997 | Heller |
| 5,695,501 A | 12/1997 | Carol et al. |
| 5,713,858 A | 2/1998 | Heruth et al. |
| 5,755,697 A | 5/1998 | Jones et al. |
| 5,776,064 A | 7/1998 | Kalfas et al. |
| 5,776,143 A | 7/1998 | Adams et al. |
| 5,776,144 A | 7/1998 | Leysieffer et al. |
| 5,788,713 A | 8/1998 | Dubach et al. |
| 5,807,033 A | 9/1998 | Benway |
| 5,809,694 A | 9/1998 | Postans et al. |
| 5,810,712 A | 9/1998 | Dunn |
| 5,817,106 A | 10/1998 | Real |
| 5,823,975 A | 10/1998 | Stark et al. |
| 5,833,627 A | 11/1998 | Shmulewitz et al. |
| 5,843,150 A | 12/1998 | Dreessen et al. |
| 5,851,183 A | 12/1998 | Bucholz |
| 5,865,817 A | 2/1999 | Moenning et al. |
| 5,865,842 A | 2/1999 | Knuth et al. |
| 5,871,445 A | 2/1999 | Bucholz |
| 5,871,487 A | 2/1999 | Warner et al. |
| 5,873,822 A | 2/1999 | Ferre et al. |
| 5,891,034 A | 4/1999 | Bucholz |
| 5,891,157 A | 4/1999 | Day et al. |
| 5,927,277 A | 7/1999 | Baudino et al. |
| 5,950,629 A | 9/1999 | Taylor et al. |
| 5,954,687 A | 9/1999 | Baudino |
| 5,957,933 A | 9/1999 | Yanof et al. |
| 5,957,934 A | 9/1999 | Rapoport et al. |
| 5,964,705 A | 10/1999 | Truwit et al. |
| 5,980,535 A | 11/1999 | Barnett et al. |
| 5,984,930 A | 11/1999 | Maciunas et al. |
| 5,993,463 A | 11/1999 | Truwit |
| 5,997,471 A | 12/1999 | Gumb et al. |
| 6,006,126 A | 12/1999 | Cosman |
| 6,018,094 A | 1/2000 | Fox |
| 6,021,343 A | 2/2000 | Foley et al. |
| 6,024,729 A | 2/2000 | Dehdashtian et al. |
| 6,030,223 A | 2/2000 | Sugimori |
| 6,039,725 A | 3/2000 | Moenning et al. |
| 6,042,540 A | 3/2000 | Johnston et al. |
| 6,044,304 A | 3/2000 | Baudino |
| 6,058,323 A | 5/2000 | Lemelson |
| 6,071,288 A | 6/2000 | Carol et al. |
| 6,076,008 A | 6/2000 | Bucholz |
| 6,079,681 A | 6/2000 | Stern et al. |
| 6,110,182 A | 8/2000 | Mowlai-Ashtiani |
| 6,117,143 A | 9/2000 | Hynes et al. |
| 6,120,465 A | 9/2000 | Guthrie et al. |
| 6,135,946 A | 10/2000 | Konen et al. |
| 6,179,826 B1 | 1/2001 | Aebischer et al. |
| 6,195,577 B1 | 2/2001 | Truwit et al. |
| 6,206,890 B1 | 3/2001 | Truwit |
| 6,210,417 B1 | 4/2001 | Baudino et al. |
| 6,231,526 B1 | 5/2001 | Taylor et al. |
| 6,236,875 B1 | 5/2001 | Bucholz et al. |
| 6,238,402 B1 | 5/2001 | Sullivan, III et al. |
| 6,254,532 B1 | 7/2001 | Paolitto et al. |
| 6,257,407 B1 | 7/2001 | Truwit et al. |
| 6,261,300 B1 | 7/2001 | Carol et al. |
| 6,267,769 B1 | 7/2001 | Truwit |
| 6,267,770 B1 | 7/2001 | Truwit |
| 6,273,896 B1 | 8/2001 | Franck et al. |
| 6,282,437 B1 | 8/2001 | Franck et al. |
| 6,290,644 B1 | 9/2001 | Green, II et al. |
| 6,298,262 B1 | 10/2001 | Franck et al. |
| 6,315,770 B1 | 11/2001 | de la Torre et al. |
| 6,321,104 B1 | 11/2001 | Gielen et al. |
| 6,327,491 B1 | 12/2001 | Franklin et al. |
| 6,356,792 B1 | 3/2002 | Errico et al. |
| 6,368,329 B1 | 4/2002 | Truwit |
| 6,400,992 B1 | 6/2002 | Borgersen et al. |
| 6,457,963 B1 | 10/2002 | Tawara et al. |
| 6,482,182 B1 | 11/2002 | Carroll et al. |
| 6,488,620 B1 | 12/2002 | Segermark et al. |
| 6,491,699 B1 | 12/2002 | Henderson et al. |
| 6,529,765 B1 | 3/2003 | Franck et al. |
| 6,537,232 B1 | 3/2003 | Kucharczyk et al. |
| 6,546,277 B1 | 4/2003 | Franck et al. |
| 6,546,279 B1 | 4/2003 | Bova et al. |
| 6,547,795 B2 | 4/2003 | Schneiderman |
| 6,556,857 B1 | 4/2003 | Estes et al. |
| 6,609,020 B2 | 8/2003 | Gill |
| 6,610,100 B2 | 8/2003 | Phelps et al. |
| 6,632,184 B1 | 10/2003 | Truwit |
| 6,655,014 B1 | 12/2003 | Babini |
| 6,662,035 B2 | 12/2003 | Sochor |
| 6,676,669 B2 | 1/2004 | Charles et al. |
| 6,706,050 B1 | 3/2004 | Giannadakis |
| 6,726,678 B1 | 4/2004 | Nelson et al. |
| 6,746,471 B2 | 6/2004 | Mortier et al. |
| 6,752,812 B1 | 6/2004 | Truwit |
| 6,765,122 B1 | 7/2004 | Stout |
| 6,773,443 B2 | 8/2004 | Truwit et al. |
| 6,782,288 B2 | 8/2004 | Truwit et al. |
| 6,802,323 B1 | 10/2004 | Truwit et al. |
| 6,902,569 B2 | 6/2005 | Parmer et al. |
| 6,913,478 B2 | 7/2005 | Lamirey |
| 6,944,895 B2 | 9/2005 | Truwit |
| 6,960,216 B2 | 11/2005 | Kolb et al. |
| 7,204,840 B2 | 4/2007 | Skakoon et al. |
| 7,366,561 B2 | 4/2008 | Mills et al. |
| 7,479,146 B2 | 1/2009 | Malinowski |
| 2001/0014771 A1 | 8/2001 | Truwit et al. |
| 2001/0027271 A1 | 10/2001 | Franck et al. |
| 2001/0037524 A1 | 11/2001 | Truwit |
| 2002/0010479 A1 | 1/2002 | Skakoon et al. |
| 2002/0019641 A1 | 2/2002 | Truwit |
| 2002/0022847 A1 | 2/2002 | Ray et al. |
| 2002/0052610 A1 | 5/2002 | Skakoon et al. |
| 2002/0077646 A1 | 6/2002 | Truwit et al. |
| 2002/0156372 A1 | 10/2002 | Skakoon et al. |
| 2003/0079287 A1 | 5/2003 | Truwit |
| 2003/0187351 A1 | 10/2003 | Franck et al. |
| 2003/0208122 A1 | 11/2003 | Melkent et al. |
| 2004/0026161 A1 | 2/2004 | Takatsuka et al. |
| 2004/0059260 A1 | 3/2004 | Truwit |
| 2004/0176750 A1 | 9/2004 | Nelson et al. |
| 2004/0243147 A1 | 12/2004 | Lipow |
| 2004/0255991 A1 | 12/2004 | Truwit et al. |
| 2004/0260323 A1 | 12/2004 | Truwit et al. |
| 2004/0267284 A1 | 12/2004 | Parmer et al. |
| 2006/0122627 A1 | 6/2006 | Miller et al. |

| | | | |
|---|---|---|---|
| 2006/0192319 | A1 | 8/2006 | Solar |
| 2006/0195119 | A1 | 8/2006 | Mazzocchi et al. |
| 2007/0250078 | A1 | 10/2007 | Stuart |
| 2007/0299427 | A1 | 12/2007 | Yeung et al. |
| 2008/0004632 | A1 | 1/2008 | Sutherland et al. |

FOREIGN PATENT DOCUMENTS

| | | |
|---|---|---|
| DE | 3937052 | 5/1990 |
| DE | 29612100 | 9/1996 |
| DE | 19726141 | 1/1999 |
| DE | 19826078 | 8/1999 |
| DE | 29612100 | 8/1999 |
| DE | 19808220 | 9/1999 |
| DE | 19820808 | 9/1999 |
| DE | 19820808 | 11/1999 |
| DE | 19826078 | 11/1999 |
| EP | 0386936 | 5/1990 |
| EP | 0386936 | 9/1990 |
| EP | 0427358 | 5/1991 |
| EP | 0724865 | 5/1991 |
| EP | 0609085 | 8/1994 |
| EP | 0724865 | 8/1996 |
| EP | 0832611 | 4/1998 |
| EP | 0904741 | 3/1999 |
| GB | 2237993 | 5/1991 |
| GB | 2329473 | 4/1998 |
| GB | 2329473 | 3/1999 |
| GB | 2346573 | 8/2000 |
| WO | WO-8809151 | 12/1988 |
| WO | WO-9522297 | 8/1995 |
| WO | WO-9610368 | 4/1996 |
| WO | WO-9633766 | 10/1996 |
| WO | WO-9703609 | 2/1997 |
| WO | WO-9721380 | 6/1997 |
| WO | WO-9742870 | 11/1997 |
| WO | WO-9817191 | 4/1998 |
| WO | WO-9825535 | 6/1998 |
| WO | WO-9851229 | 11/1998 |
| WO | WO-0001316 | 1/2000 |
| WO | WO-0018306 | 1/2000 |
| WO | WO-0018306 | 4/2000 |
| WO | WO-0124709 | 4/2001 |
| WO | WO-0149197 | 7/2001 |
| WO | WO-0176498 | 7/2001 |
| WO | WO-0176498 | 10/2001 |
| WO | WO-2004026161 A2 | 4/2004 |

OTHER PUBLICATIONS

"MicroTargeting® Precision Guidance Using Microelectrode Recording", (Aug. 15, 2003),5 pgs.
International Search Report and Written Opinion for PCT/US05/43651 mailed May 8, 2008.
Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.
"Cross-Hairs Kit", Elekta Instruction for Use Brochure, pp. 1-5.
"CRWTM—Tyco Healthcare Radionics", Tyco Products Brochure, pp. 1-7.
"Fathom Remote Introducer", Image-Guided Neurologics, Inc. CNS Hynes Convention Center, (Oct. 30-Nov. 4, 1999), 2 pgs.
"Leksell Sterotatic System", Elekta Products Brochure, pp. 1-6.
"Possible Existence of Common Internalization Mechanisms among Arginine-rich Peptides", Suzuki, T. et al., Journal of Biological Chemistry, vol. 277, No. 4 (2002) pp. 2437-2443.
Allison, S., et al., "Microchannel Plate Intensifier Response in Traverse Magnetic Field", Electronic Letters, 26, (Jun. 7, 1990), 770-771.
Drake, J. M., et al., "ISG Viewing Wand System" Neurosurgery, 34 (6), (Jun. 1994), pp. 1094-1097.
Dyer, P. V., et al., "The ISG Viewing Wand: an application to atlanto-axial surgery using the Le Fort I maxillary osteotomy", British Journal of Oral & Maxillofacial Surgery, 33 (1995), pp. 370-374.
Franck, Joel, et al., "microTargeting® Platform incorporating StarFix™ guidance", microTargeting, 3 pgs.
Franck, Joel, et al., "microTargeting® Platform System incorporating StarFix™ guidance", microTargeting, p. 44.
Gehring, W. J., "Homeodomain Proteins", Annu. Rev. Biochem., vol. 63 (1997) pp. 487-526.
Gillies, G., et al., "Magnetic Manipulation Instrumentation for Medical Physics Research", Review of Scientific Instruments, 65 (3), Review Article, (Mar. 1994), 533-562.
Grady, M. S., "Magnetic Stereotaxis System for Neurosurgical Procedures", Proceedings of the 37th International Instrumentation symposium, (May 5-9, 1991), pp. 665-675.
Grady, M. S., et al., "Initial Experimental Results of a New Stereotaxic Hyperthermia System", American College of Surgeons, Surgical Forum, vol. XXXIX, Neurological Surgery, (1988), pp. 507-509.
Grady, M. S., et al., "Magnetic Stereotaxis: A Technique to Deliver Stereotactic Hyperthermia", Neurosurgery, 27 (6), (1990), pp. 1010-1016.
Grady, M. S., et al., "Preliminary experimental investigation of in vivo magnetic manipulation: Results and potential application in hyperthermia" Medical Physics, 16 (2), (Mar./Apr. 1989), pp. 263-272.
Grady, M., et al., "Nonlinear Magnetic Stereotaxis: Three-Dimensional, in vivo Remote Magnetic Manipulation of a Small Object in Canine Brain", Medical Physics, 17 (3), (May/Jun. 1990), pp. 405-415.
Hata, N., et al., "Needle Insertion Manipulator for CT- and MR-Guided Stereotactic Neurosurgery", Interventional MR: Techniques and Clinical Experience, St. Louis : London : Mosby ; Martin Dunitz, F. Jolesz and I. Young, eds., (1998), pp. 99-106.
Hirschberg, H., et al., "Image-guided neurosurgery—MR compatible stereotactic equipment", http://www.medinnova.no/English/P51466ster.html, (Mar. 29, 2001), 1 pg. (viewed website on Mar. 29, 2001).
Hirschberg, Henry, et al., "Image-guided neurosurgery", stereotactic equipment for MR imaging, http://www.medinnova.no/English/P51466ster.html, (Observed Mar. 8, 2002), 1 page.
Howard III, M. A., et al., "Magnetic Neurosurgery: Image-Guided Remote-Controlled Movement of Neurosurgical Implants", Clinical Neurosurgery, (1995), pp. 382-391.
Howard III, M. A., et al., "Review of Magnetic Neurosurgery Research", Journal of Image Guided Surgery, 1 (6), (1995), pp. 295-299.
Howard, M. A., et al., "Magnetic Movement of a Brain Thermoceptor", Neurosurgery, 24 (3), (Mar. 1989), pp. 444-448.
Howard, M. A., et al., "Magnetic Neurosurgery", Proceedings of the Meeting of the American Society for Stereotactic and Functional Neurosurgery, (Mar. 8-11, 1995), pp. 102-107.
Lawson, M. A., et al., "Near Real-Time Bi-planar Fluoroscopic Tracking System for the Video Tumor Fighter", SPIE, vol. 1445 Image Processing, (1991), pp. 265-275.
Leggett, W.B., et al., "Surgical Technology—The Viewing Wand: A New System for Three-Dimensional Computed Tomography-Correlated Intraoperative Localization", Current Surgery, (Dec. 1991), pp. 674-678.
Malison, R. T., et al., "Computer-Assisted Coregistration of Multislice SPECT and MR Brain Images by Fixed External Fiducials", Journal of Computer Assisted Tomography, 17 (6) (1993) pp. 952-960.
Mannervik, M., "Target genes of homeodomain proteins", BioEssays vol. 21.4 (Apr. 1999) pp. 267-270.
McNeil, R. G., et al., "Characteristics of an Improved Magnetic-Implant Guidance System", IEEE Transactions on Biomedical Engineering, 42 (8), (Aug. 1995), pp. 802-808.
McNeil, R. G., et al., "Functional Design Features and Initial Performance Characteristics of a Magnetic-Implant Guidance System for Stereotactic Neurosurgery", IEEE Transactions on Biomedical Engineering, 42 (8), pp. 793-801.

Meeker, D., et al., "Optimal Realization of Arbitrary Forces in a Magnetic Stereotaxis System," IEEE Transactions on Magnetics, 32 (2), (Mar. 1996), 320-328.

Molloy, J. A., et al., "Experimental Determination of the Force Required for Insertion of a Thermoseed Into Deep Brain Tissues", *Annals of Biomedical Engineering*, 18 (3), (1990), pp. 299-313.

Molloy, J. A., et al., "Thermodynamics of movable inductively heated seeds for the treatment of brain tumors", *Medical Physics*, 18 (4), (Jul./Aug. 1991), pp. 794-803.

Oliver, L., "Cup-And-Ball Chemopallidectomy Apparatus", (1958), p. 410.

Patikoglou, G. et at., "Eukaryotic Transcription Factor-DNA Complexes", Annual Review of Biophysics and Biomolecular Structure vol. 26 (1997) pp. 289-325.

Quate, E., et al., "Goniometric Motion Controller for the Superconducting Coil in a Magnetic Stereotaxis System", IEEE Transactions on Biomedical Engineering, 38 (9), (Sep. 1991), 899-905.

Ramos, P. A., et al., "Electro-optic imaging chain for a biplanar fluoroscope for neurosurgery: magnetic field sensitivity and contrast measurements" *Optical Engineering*, 32 (7), (Jul. 1993), pp. 1644-1656.

Ramos, P. A., et al., "Low-dose, magnetic field-immune, bi-planar fluoroscopy for neurosurgery", *SPIE Medical Imaging V: Image Physics*, vol. 1443, (1991), pp. 160-170.

Ramos, P. A., et al., "Microchannel Plate Image Intensifier Electron Dynamics in Magnetic Field", *Electronics Letters*, 27 (18), (Aug. 29, 1991), pp. 1636-1638.

Ritter, R. C., et al., "Magnetic Stereotaxis: An Application of Magnetic Control Technology to the Needs of Clinical Medicine", *Proc. of the MAG'95 Industrial Conf. and Exhibition, Technomic Pub. Co.*, Lancaster, PA., Allaire P., ed., 1995, pp. 186-193.

Ritter, R. C., et al., "Magnetic Stereotaxis: Computer-Assisted Image-Guided Remote Movement of Implants in the Brain" *Computer-Integrated Surgery: Technology and Clinical Applications*, MIT Press, (1996), pp. 363-369.

Sandeman, D. S., et al., "Advances in image-directed neurosurgery: Preliminary experience with the ISG Viewing Wand compared with the Leksell G frame", *British Journal of Neurosurgery*, 8, (1999), pp. 529-544.

Stein, S. et al., "Checklist: Vertebrate homeobox genes", Mechanisms of Development, vol. 55, No. 1 (Mar. 1996) pp. 91-108.

Szikora, Istvan, et al., "Endovascular Treatment of Experimental Aneurysms with Liquid Polymers: The Protective Potential of Stents", *Neurosurgery*, 38 (2), (Feb. 1996), pp. 339-347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1, (Feb. 1996) pp. 62-68.

Yeh, H.-S., et al., "Implantation of intracerebral depth electrodes for monitoring seizures using the Pelorus stereotactic system guided by magnetic resonance imaging", *J. Neurosurg.*, 78, (1993), pp. 138-141.

Zinreich, S. J., et al., "Frameless Sterotaxic Integration of CT Imaging Data: Accuracy and Initial Applications", *Radiology*, 188 (3), (1993), pp. 735-742.

Supplementary European Search Report mailed Oct. 26, 2009 for EP05852969 filed Dec. 6, 2005 claiming benefit of U.S. Appl. No. 11/005,907, filed Dec. 5, 2004.

European Office Action mailed Jan. 22, 2010 for European Application No. 05 852 969.4.

* cited by examiner

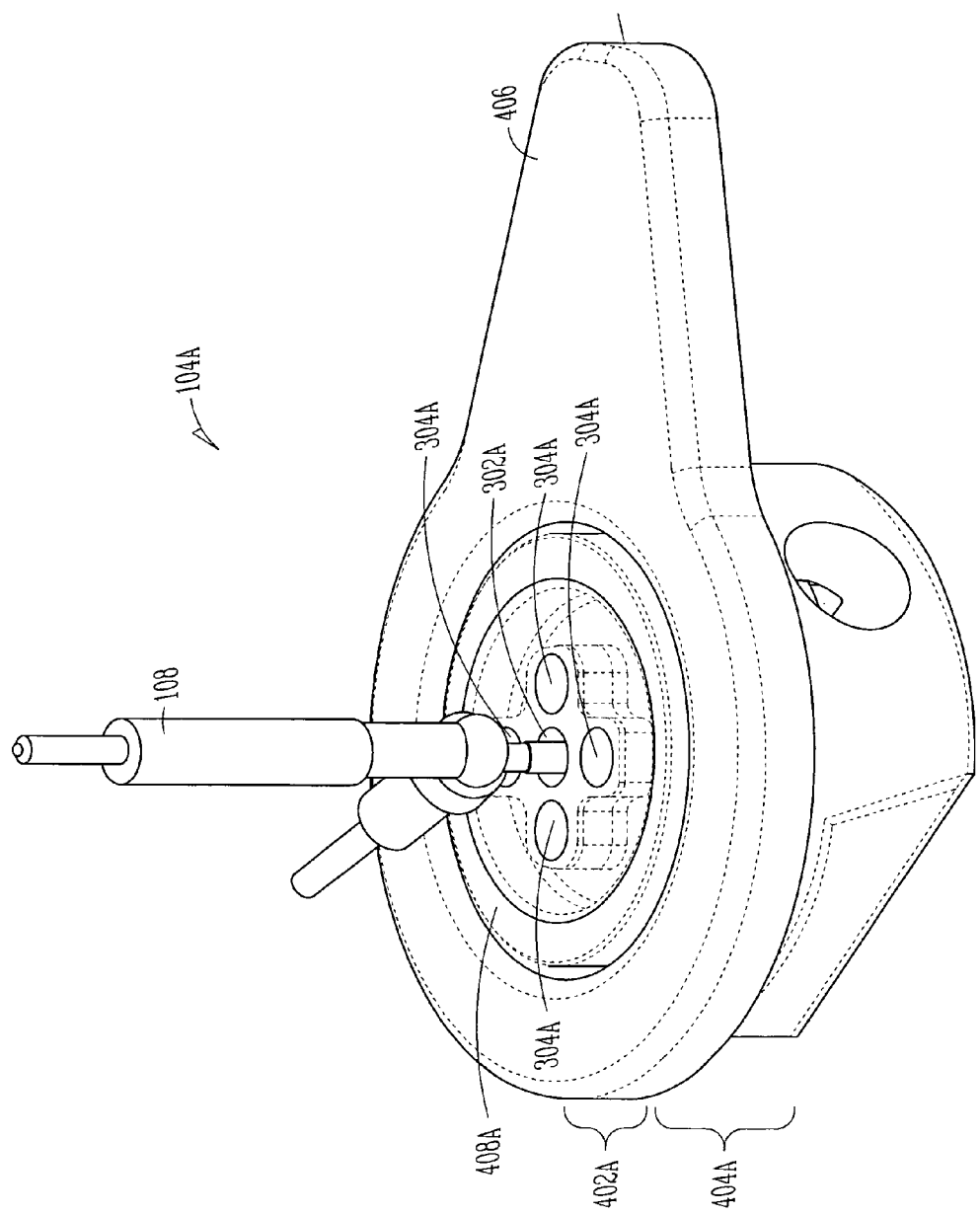

MULTIPLE INSTRUMENT RETAINING ASSEMBLY AND METHODS THEREFOR

CROSS-REFERENCE TO RELATED APPLICATIONS

This patent application is a continuation-in-part of, and claims priority to, commonly-assigned U.S. patent application Ser. No. 11/005,607 to Solar et al., entitled "INSTRUMENT GUIDING STAGE APPARATUS AND METHOD FOR USING THE SAME," filed on Dec. 4, 2004, now U.S. Pat. No. 7,497,863, which is incorporated herein by reference in its entirety.

This patent application is also related to U.S. patent application Ser. No. 11/005,605 to Miller et al., entitled "MULTI-LUMEN INSTRUMENT GUIDE," filed on Dec. 4, 2004, which is also incorporated herein by reference in its entirety.

TECHNICAL FIELD

This patent document pertains generally to the use of surgical instruments or observation tools in neurosurgery. More particularly, but not by way of limitation, this patent document pertains to a multiple instrument retaining assembly and methods therefor.

BACKGROUND

In the treatment of some diseases or defects associated with a patient, it has been found necessary to access specific targets within the patient. For example, in neurosurgery, it have been found necessary to access specific targets within the patient's brain. In neurosurgery, the specific targets are typically located and identified by one of a number of techniques. Sometimes the target can be visualized on computer tomography (CT) or magnetic resonance imaging (MRI). Other times, the position of the target must be determined by its relationship to an anatomic structure viewable on scanning using conventional radiographs or by ventriculography.

Once a target has been identified, neurosurgery involves making a drill hole in the relatively thick bony structure surrounding the brain (i.e., the skull). The drill hole is made by a surgeon at a desired entry point using a surgical drill. The surgeon then guides (e.g., using trajectory guide tubes) one or more surgical instruments or observation tools (e.g., electrodes—recording or stimulating, cannulas, needles, biopsy instruments, catheters or other types of probes or devices) through the entry hole to the specific targets within the brain. Based on the fact that, to some extent, considerable relative movements between the instruments or tools and the targeted positions on the body of the patient can occur with hand-guided instruments or tools, and that these relative movements are in part associated with considerable risks for the patient (e.g., damage to healthy brain tissue), it is desirable to anchor these instruments or tools securely relative to the body while still being able to guide them in three dimensions within certain limits. To prevent relative movements between the body of the patient and the surgical instruments or observation tools, a drive and trajectory guide assembly mechanically coupled to the patient may be utilized.

Using a secured drive and trajectory guide assembly, and in some examples, one or more guide tubes, the instruments or tools may be precisely advanced into the brain until the operable portion of each of the instruments or tools is positioned adjacent the site of interest (i.e., the site of the brain to be operated on). Once the operable portion of each instrument or tool is positioned as desired, or during the advancement of each instrument or tool, selective position retainment of such instruments or tools is often needed. In addition, selective positions of the guide tubes may need to be retained.

Unfortunately, many of the currently available assemblies used to guide or retain neurosurgical instruments, observations tools, or guide tubes have one or more of the following drawbacks: being expensive to manufacture (e.g., due to precise tolerance requirements); retaining a limited number of instruments, tools, or tubes; requiring actuation at multiple sites; requiring a relatively large clamping force be applied to one or more actuators; or not providing a user with a good "feel" of the actual retainment force being applied to each instrument, tool, or tube (e.g., due to large bending or compression forces required for retainment).

It is with this knowledge of the foregoing state of the technology that the present multiple instrument retaining assembly and methods therefor have been conceived and are now set forth in text and drawings associated with this patent document.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in this patent document.

FIG. 4A is an isometric view illustrating, among other things, a portion of a retaining assembly and an instrument, as constructed in accordance with at least one embodiment.

DETAILED DESCRIPTION

The following detailed description includes references to the accompanying drawings, which form a part of the detailed description. The drawings show, by way of illustration, specific embodiments in which the present assemblies and methods may be practiced. These embodiments, which are also referred to herein as "examples," are described in enough detail to enable those skilled in the art to practice the present assemblies and method. The embodiments may be combined or varied, other embodiments may be utilized or structural or logical changes may be made without departing from the scope of the present assemblies and methods. It is also to be understood that the various embodiments of the present assemblies and methods, although different, are not necessarily mutually exclusive. For example, a particular feature, structure or characteristic described in one embodiment may be included within other embodiments. The following detailed description is, therefore, not to be taken in a limiting sense, and the scope of the present assemblies and methods are defined by the appended claims and their legal equivalents.

In this document the terms "a" or "an" are used to include one or more than one; the term "or" is used to refer to a nonexclusive or, unless otherwise indicated; the term "instrument" is used to refer to any instrument which can be used in a neurosurgical procedure such as surgical instruments, observation tools, or trajectory guide tubes; and the term "subject" is used to include the term "patient." In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Introduction and Examples

Currently, there is no cure for some neurological disorders, such as Parkinson's Disease (referred to as "PD") or essential tremor (referred to as "ET"). However, the symptoms associated with these diseases are treatable, such as by surgical intervention. One primary type of surgery is neurostimulation, which works by disrupting the uncontrolled firing of brain cells that causes the symptoms associated with PD and ET. When surgery is chosen to help control the symptoms associated with, for example, PD or ET, surgeons use three-dimensional scanning techniques (as discussed above) to recognize one or more problem areas in the brain. After the problem area(s) are recognized, one or more instruments are guided to such areas.

Figure 1:
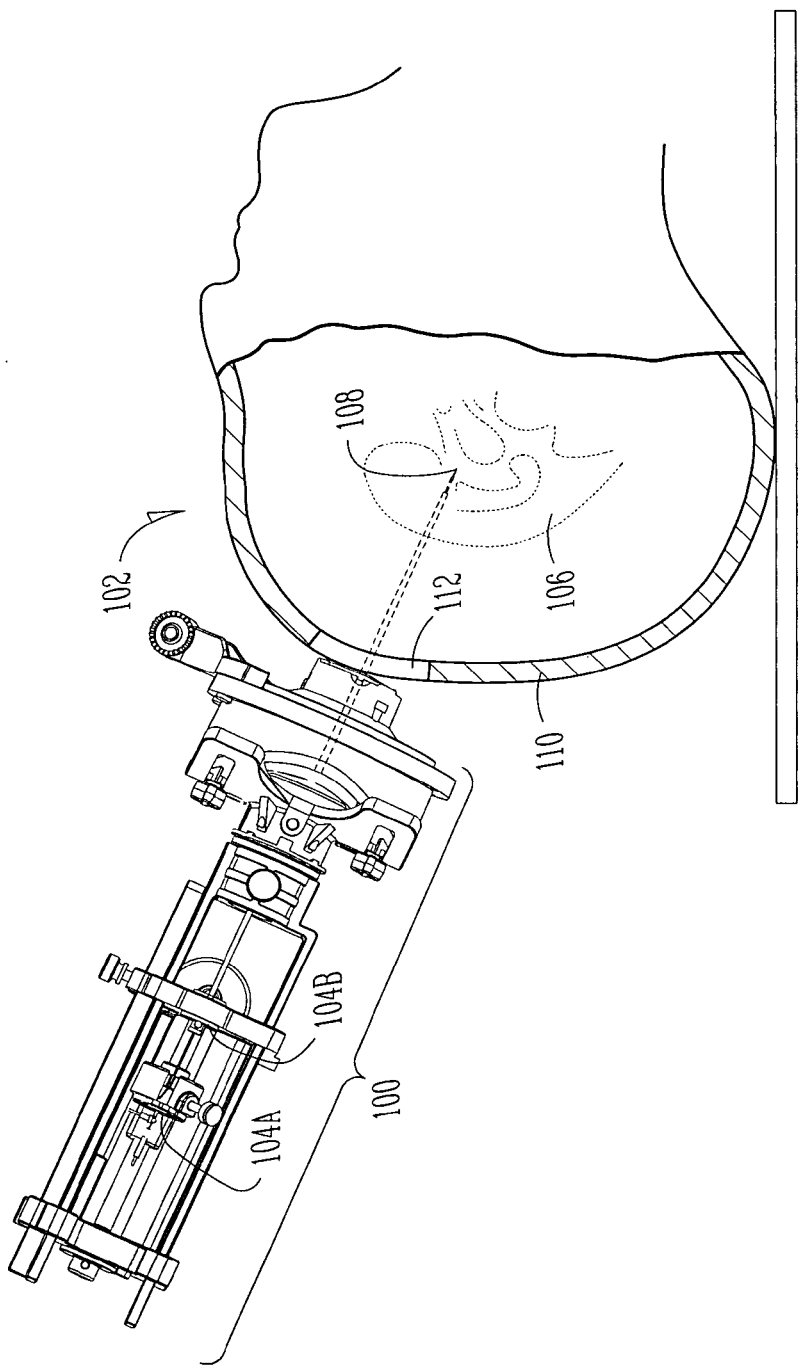
FIG. 1 is a schematic view illustrating a drive and trajectory guide assembly, an instrument, and an environment in which the drive and trajectory guide assembly and instrument may be used, as constructed in accordance with at least one embodiment.
Figure 2:
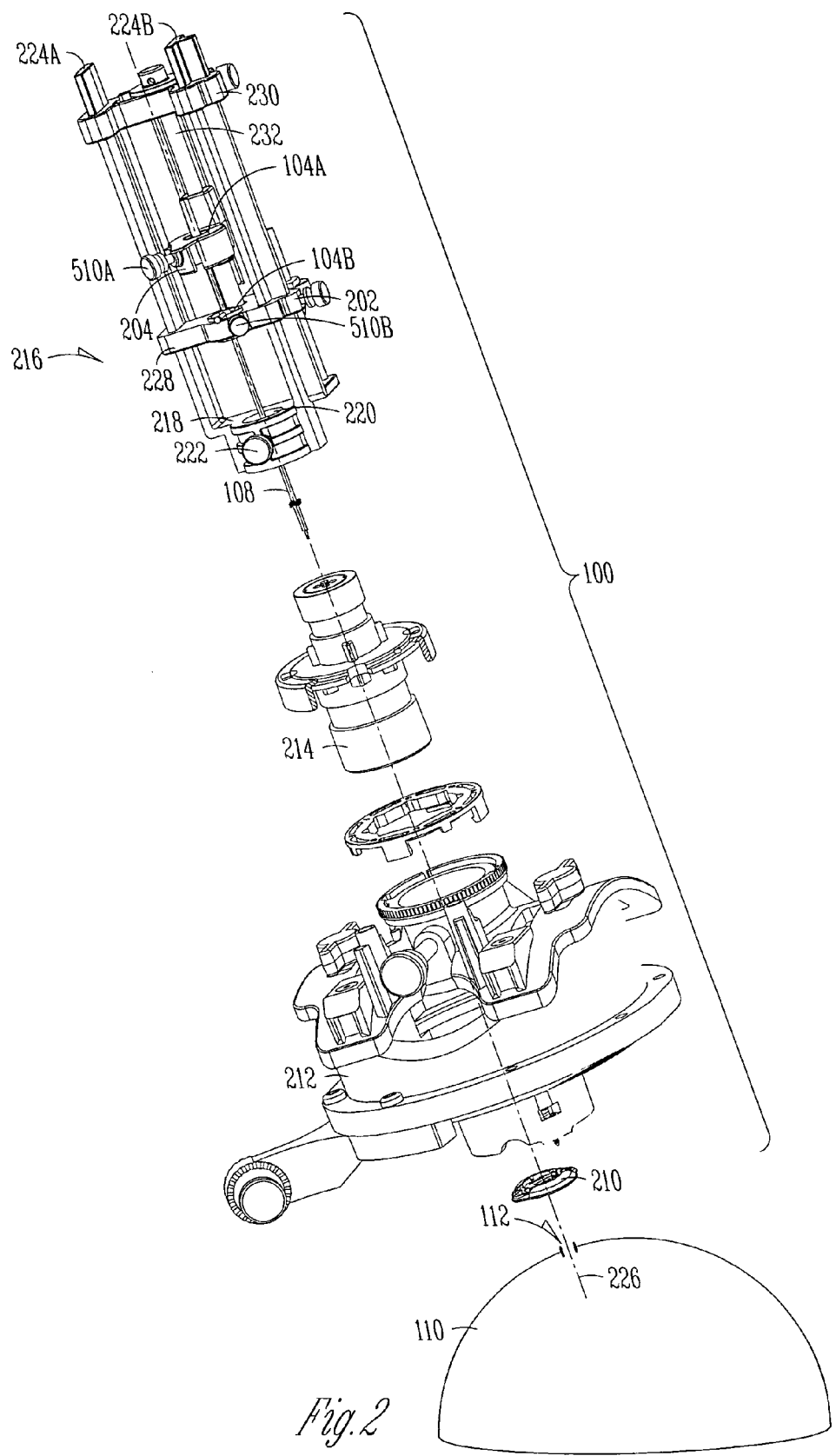
FIG. 2 is an exploded isometric view illustrating a view of a drive and trajectory guide assembly and an instrument, as constructed in accordance with at least one embodiment.

Neurostimulation is a technique involving the insertion of a recording electrode (for recording brain signals) and thereafter (or in conjunction with) the accurate delivery and permanent implantation of a stimulation electrode (for providing stimulating pulses) in the brain. Advantageously, the drive and trajectory guide assembly 100 shown in FIGS. 1-2 allows for the precise advancement of one or more recording or stimulation electrodes (or other instruments) into the brain until the operable portion of each electrode is positioned adjacent the site of interest. In addition, the trajectory guide assembly 100 of FIGS. 1-2 provides selective position retainment of the electrodes (via one or more retaining assemblies 104A, 104B) during the implantation procedure. After the stimulation electrodes are appropriately positioned, each electrode is connected to a battery operated implantable pulse generator (referred to as "IPG") located under the skin of a subject's chest. Much like a cardiac pacemaker, mild electrical current is delivered by the IPG, through the stimulation electrodes, and to a target areas in the subject's brain 106.

Although neurostimulation for the treatment of PD or ET has been discussed, the present assemblies and methods are not so limited. For example, the drive and trajectory guide assembly 100 shown in FIGS. 1-2 is important to the success of a number of other neurological surgical procedures, in which accurate insertion and retainment of instruments is very important, including: neuroendoscopy, brain biopsy or stereotactic brain biopsy, catherization, placement of brain transplant tissue, placement of transducers for brain function monitoring, or the administration of pharmaceuticals within the brain. In addition, the present assemblies and methods may be used to treat or aid in the treatment of, among other things, brain tumors, spinal disorders, intracranial vascular surgery, carotid artery surgery and endovascular treatment, surgical treatment for epilepsy including vagal nerve stimulation, spinal tumors and vascular lesions, surgical treatment for trigeminal neuralgia and hemifacial spasm, surgery for pituitary tumors, multidisciplinary treatment of complex skull base tumors, or multidisciplinary treatment of complex peripheral nerve disorders.

The assemblies and methods herein provide numerous advantages over currently available assemblies used to guide or retain neurosurgical instruments including employment of a plurality of retainment holders, such as five retainment holders, driven by one actuation means. In addition, the present assemblies are inexpensive to manufacture (e.g., may comprise molded plastic parts), yet provide a user with a good "feel" of the actual retainment force being applied to each instrument (e.g., due to direct force application without the presence of large bending or compression forces). Several other advantages are also made possible by the present assemblies and methods including the ability to be used with instruments of varying sizes (e.g., instrument diameters). Yet another advantage is that the present assembly does not require a large actuation force for the retainment of the instruments contained therein.

FIG. 1 illustrates a side view of a subject 102 on which a drive and trajectory guide assembly 100 including one or more multiple instrument retaining assemblies 104A, 104B is mounted. Drive and trajectory guide assembly 100 is used to, among other things, precisely advance one or more instruments 108, such as an electrode or other elongated member, into a brain 106 (through a drill hole 112) until the operable portion of the instrument(s) 108 is positioned adjacent the site of interest. The drive and trajectory guide assembly 100 shown in FIG. 1 may also be used to retain the one or more instruments 108 (via retaining assemblies 104A, 104B) during the implantation procedure using a single actuator 510A, 510B means (e.g., FIG. 2) and without requiring precise toleranced components.

FIG. 2 is an exploded isometric view illustrating a drive and trajectory guide assembly 100 comprising one or more retaining assemblies 104A, 104B. As shown, an instrument immobilizer 210, configured to attached to a skull 110 around a drill hole 112, in combination with a trajectory guide 212 couples drive and trajectory guide assembly 100 to a subject 102 (FIG. 1). Specifically, instrument immobilizer 210 is screwed to skull 110, while trajectory guide 212 is also screwed to the skull outside of immobilizer 210 with separate screws. Trajectory guide 212 is further coupled to an instrument guide 214 on a top side. A top side of instrument guide 214 is configured to allow a drive assembly 216 to be coupled thereto.

In this example, drive assembly 216 includes a base 218 having a base lumen 220 configured to receive instrument guide 214. A thumb screw 222 or other fixation device extends through base 218 and into base lumen 220 (an axis of which defines an instrument trajectory 226) to engage instrument guide 214 and fixedly couple drive assembly 216 to the same. As shown, base 218 includes two guide rails 224A, 224B to which a first stage 202 is coupled. In this example, first stage 202 includes a lower portion 228 and an upper portion 230. First stage 202 also includes a first stage lumen which houses retaining assembly 104B. An actuator 510B is coupled to and extends through a portion of first stage 202 to retain one or more instruments 108 (e.g., guide tubes) extending through the first stage lumen.

A second stage 204 is moveably coupled to first stage 202. In this example, second stage 204 is slidably coupled to first stage 202 by a lead screw 232 or the like. Lead screw 232 extends between lower portion 228 and upper portion 230 and includes threads configured to mate with second stage 204. Additionally, second stage 204 includes a second stage lumen which houses retaining assembly 104A. As shown, the second stage lumen is formed by a broken ring-type structure; however, such lumen may also be defined by a continuous inner surface of second stage 204. An actuator 510A is coupled to and extends through a portion of second stage 204 to retain one or more instruments (e.g., recording electrodes) extending through the second stage lumen. A drive and trajectory guide assembly 100 having a first stage and a second stage is described in more detail in Solar et al., U.S. patent application Ser. No. 11/005,607, entitled "INSTRUMENT GUIDING STAGE APPARATUS AND METHOD FOR USING THE SAME," which was filed on Dec. 4, 2004, the disclosure of which is incorporated herein by reference in its entirety, including its description of an apparatus for advancing one or more instruments that includes, among other things, a first stage and a second stage. Optionally, multiple instruments 108 (e.g., five instruments—see FIG. 5) may be immobilized by retaining assemblies 104A, 104B.

Figure 3:
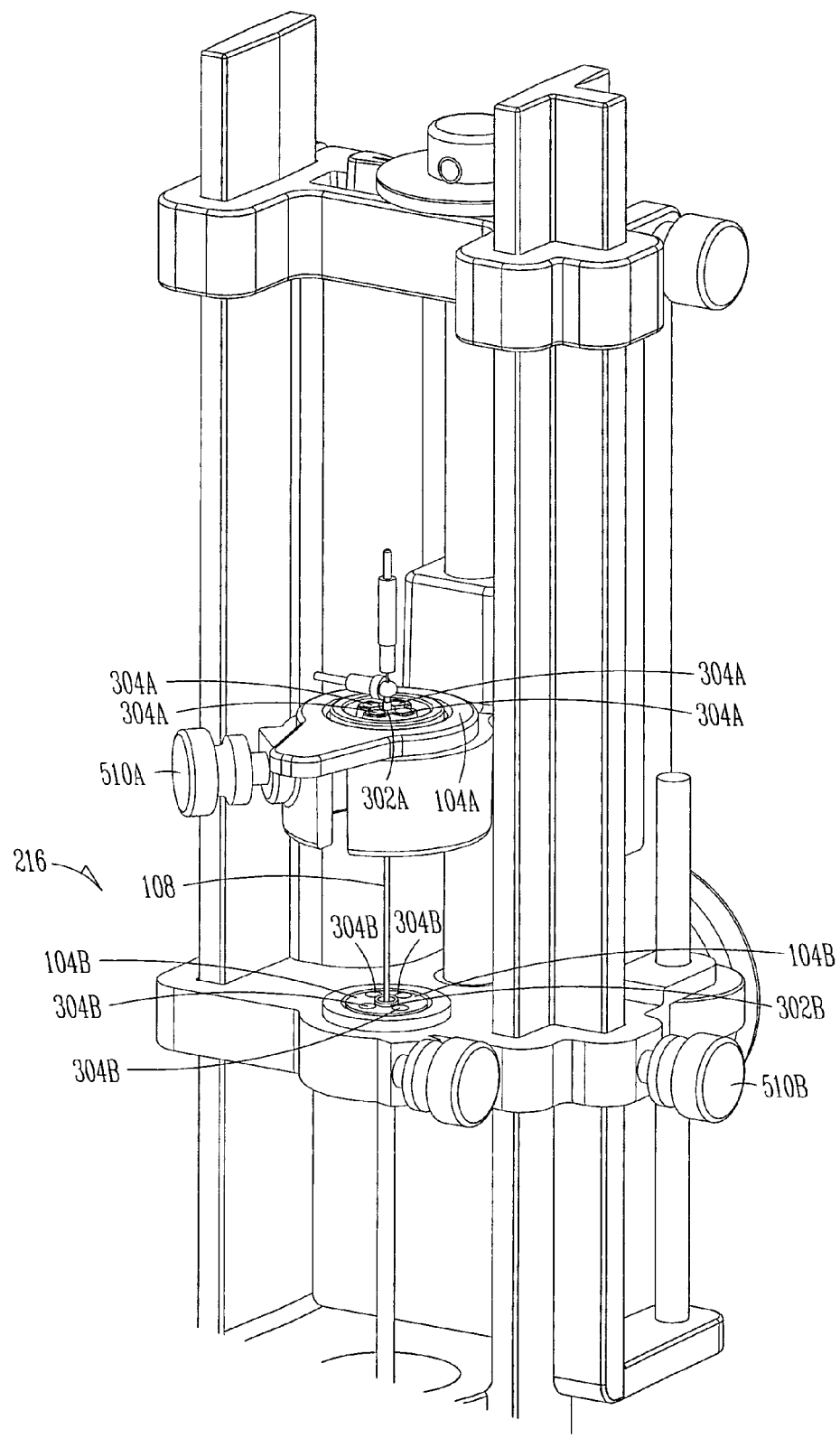
FIG. 3 is an enlarged isometric view illustrating a portion of a drive assembly and an instrument, as constructed in accordance with at least one embodiment.

FIG. 3 illustrates an example of one or more retaining assemblies 104A, 104B that allow for an instrument 108 (e.g., a recording electrode or a guide tube, respectively) to be positioned and retained in one of five tracks: a central track 302A, 302B or four parallel tracks 304A, 304B. In the example shown, parallel tracks 304A, 304B have their respective centers equidistant from a center of central track 302A, 302B. In addition, the five tracks (as shown) have equal center-to-center spacing, such as 2 mm, 2.5 mm, or 3 mm. In one such example, instrument 108 (e.g., a single recording electrode) may be positioned in any one of the five tracks and then, if additional data is required, it can be repositioned in one of the other tracks. In another example, at least five instruments 108 (see, e.g., FIG. 5) may be inserted into, and retained by, retaining assemblies 104A, 104B. Although not shown, drive and trajectory guide assembly 100 may include markings that may be utilized by an attending surgeon to orient the direction or mark the depth of instrument(s) 108 inserted into brain 106 (FIG. 1). Additionally, although five tracks are shown in FIG. 3, the present assemblies and methods are not so limited. In another example, more or less than five tracks are included in retaining assemblies 104A, 104B.

Figure 4B:
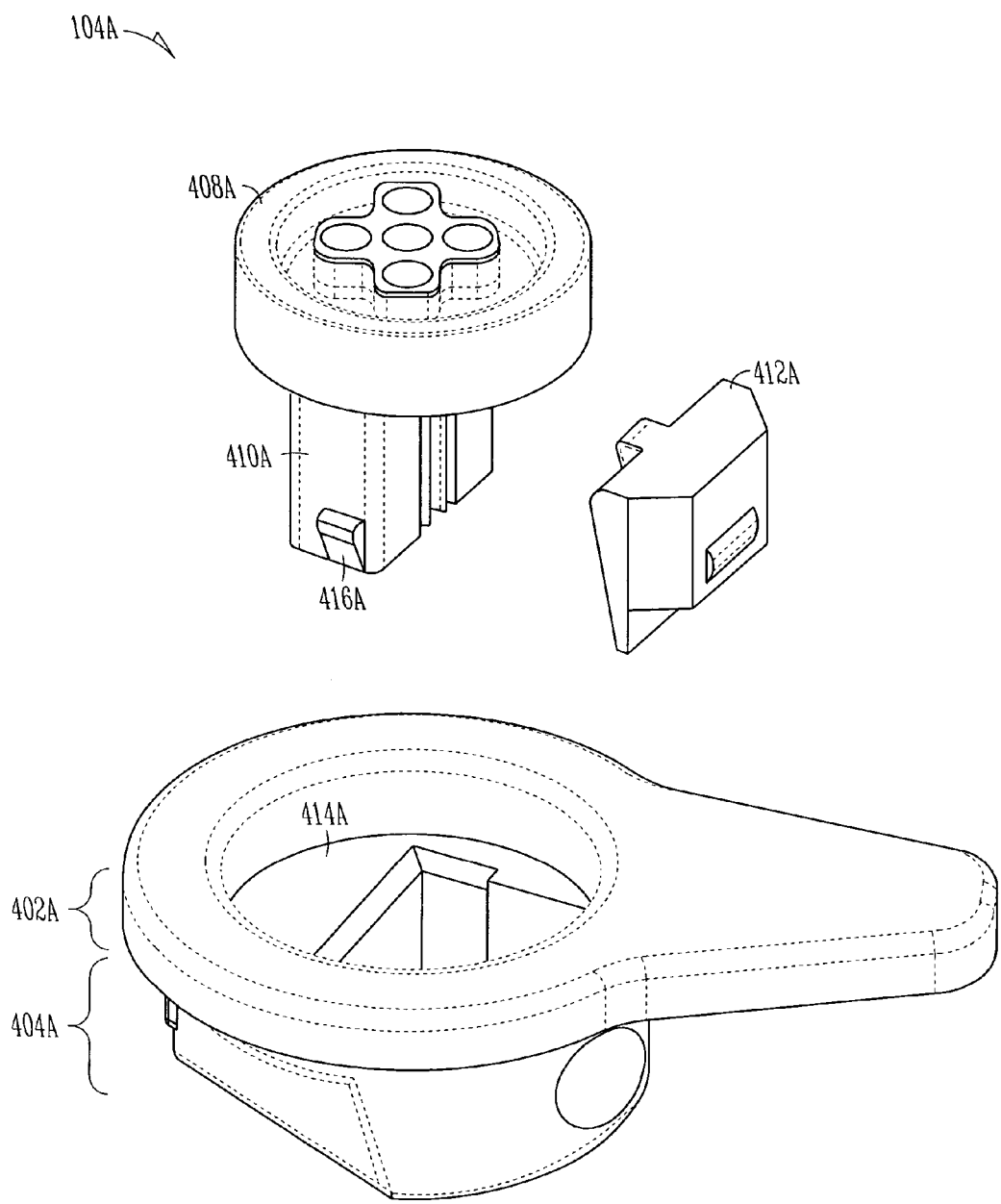
FIG. 4B is an exploded isometric view illustrating, among other things, a portion of a retaining assembly, as constructed in accordance with at least one embodiment.

FIG. 4A illustrates portions of a retaining assembly 104A couplable with a drive and trajectory guide assembly 100 (FIG. 1). As shown, retaining assembly 104A may include a cap portion 402A and a retainment portion 404A. Typically, cap portion 402A and retainment portion 404A are integral; however, such portions may also be formed separate from one another. In one example, cap portion 402A includes a handle protrusion 406 that allows a surgeon (or other user) with means to remove retaining assembly 104A, such as for subsequent introduction of one more stimulation electrodes (not shown). In another example, cap portion 402A includes a track portion 408A that provides one or more tracks (e.g., 302A, 304B) into which an instrument 108 may be inserted and thereafter retained (by retainment portion 404A). As will be discussed below, retainment portion 404A may include, among other things, a seat 410A (FIG. 4B), a first clamp member 414A (FIG. 4B), an arm member 506 (FIG. 5), a second clamp member 412A (FIG. 4B), and an actuator 510A (FIG. 5).

FIG. 4B illustrates an exploded view of portions of retaining assembly 104A of FIG. 4A. As shown in FIG. 4B, track portion 408A (of cap portion 402A) is coupled to seat 410A (of retainment portion 404A). Positioned to the right of seat 410A, is a second clamp member 412A (of retainment portion 404A) configured to be brought into engagement with seat 410A. In one example, seat 410A may include one or more tabs 416A. In one such example, two tabs 416A are positioned opposite one another between seat sides 512A and 514A (FIG. 5). Among other things, tabs 416A may provide floating coupling of seat 410A within a space defined by first clamp member 414A and arm member 506. For instance, when seat 410A is slid into engagement with first clamp member 414A and arm member 506 (FIG. 5), tabs may 416 snap-fit into floating engagement with walls of arm member 506.

Figure 5:
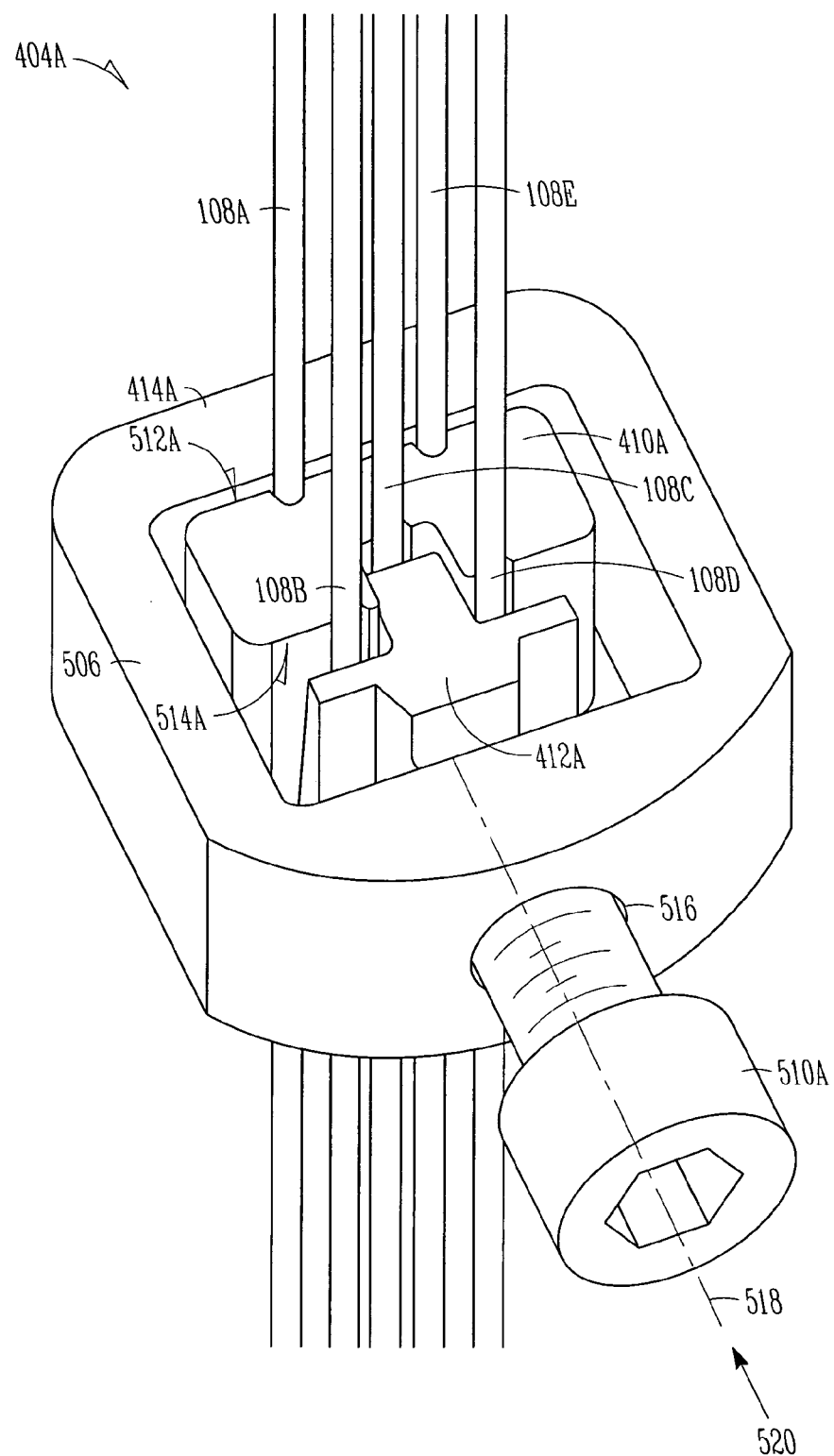
FIG. 5 is an isometric view from a top direction illustrating a retaining assembly and a plurality of instruments, as constructed in accordance with at least one embodiment.

For conceptual clarity, FIGS. 5-8B illustrate a stylized version of retaining assembly 104A, specifically retaining portion 404A, shown in FIGS. 4A-4B. Referring first to FIG. 5, which illustrates an isometric top view of retainment portion 404A for preserving a selected position of one or more instruments 108, such as recording electrodes. As shown, five instruments 108A, 108B, 108C, 108D, 108E are received by retainment portion 404A. Retainment portion 404A includes, among other things, a seat 410A, a first clamp member 414A, an arm member 506, a second clamp member 412A, and an actuator 510A. Seat 410A includes a seat first side 512A positioned opposite a seat second side 514A. In one example, first clamp member 414A is positioned adjacent seat first side 512A. In another example, arm member 506 extends from first clamp member 414A substantially toward seat second side 512A. Arm member 506 may, although not required, extend entirely around seat 410A as shown in FIG. 5. In yet another example, second clamp member 412A is positioned adjacent seat second side 514A between arm member 506 and second side 514A. In varying examples, actuator 510A is inserted into, and engaged with, an actuator receiving lumen 516. In one such example, actuator 510A includes one or more threads that mate with internal threads of actuator receiving lumen 516. As a result of the matable engagement, rotation of actuator 510A (e.g., in a clockwise direction for right-handed thread configurations) causes actuator 510A to translate (i.e., move) along axis 518.

As configured in FIG. 5, movement of actuator 510A in a first direction 520 moves seat first side 512A toward first clamp member 414A and moves second clamp member 412A toward seat second side 514A. By way of moving seat first side 512A and second clamp member 412A, instruments 108A, 108B, 108C, 108D, 108E are firmly held in place (as shown, instruments 108A, 108E are compressively held between first clamp member 414A and seat first side 512A, while instruments 108B, 108C, 108D are compressively held between second clamp member 412A and seat second side 514A), all by way of single point actuation (e.g., rotation of single actuator 510A). In addition, the configuration of FIG. 5 is such that a surgeon (or other user) is provided with a good "feel" of the actual retainment force being applied to each instrument 108 received in retainment portion 404A (due to direct force application without large bending or compressive forces being present). In contrast, configurations similar to those found in currently available retaining assemblies, such as multiple drill bit chucks, do not provide a user with a good feel of the actual retainment force being applied to each instrument. Moreover, the configuration shown in FIG. 5 is inexpensive to manufacture as a high level of dependency on tolerances does not exist.

Figure 7A:
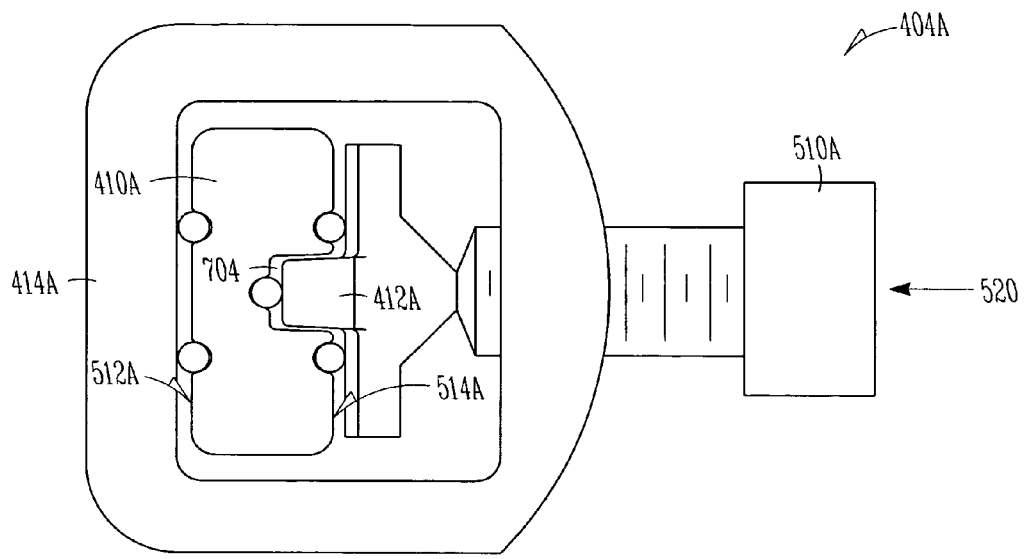
FIG. 7A is a top view illustrating a retaining assembly and a plurality of instruments, as constructed in accordance with at least one embodiment.
Figure 7B:
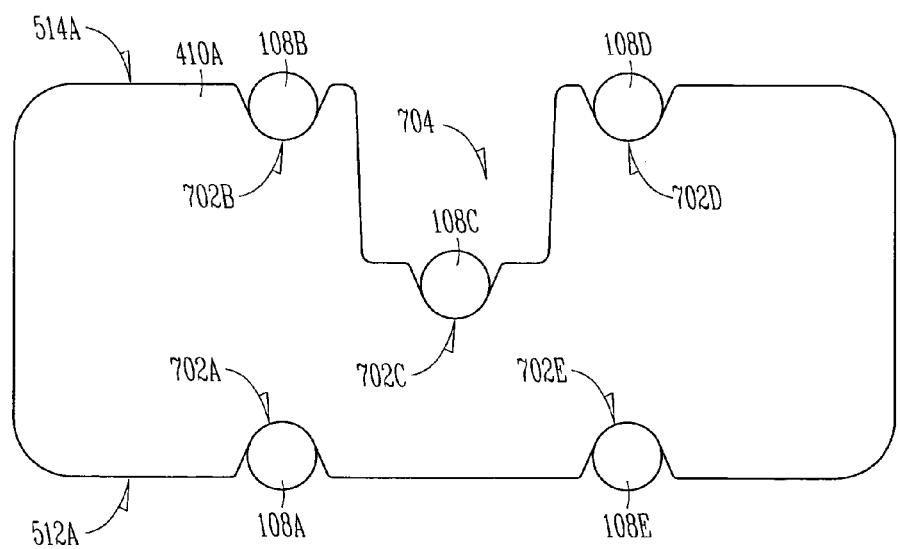
FIG. 7B is a top view illustrating a seat member of a retaining assembly and a plurality of instruments, as constructed in accordance with at least one embodiment.

Referring now to FIGS. 7A-7D, which illustrate, among other things, a top view of a seat 410A of a retainment portion 404A. Seat 410A includes a seat first side 512A and an oppositely positioned seat second side 514A. As shown, both seat first side 512A and seat second side 514A include one or more recessed portions. Specifically, seat first side 512A includes two recessed portions 702A, 702E and seat second side 514A includes three recessed portions 702B, 702C, 702D, as shown in FIG. 7B. Each recessed portion 702A, 702B, 702C, 702D, 702E is configured to provide a groove for receiving an instrument 108A, 108B, 108C, 108D, 108E, respectively. In one example, recessed portions 702A, 702B, 702C, 702D, 702E are configured to create semicircular grooves that expose at least a portion of instruments 108A, 108B, 108C, 108D, 108E outside of the perimeter of seat 410A.

Although not required, two recessed portions 702B, 702D disposed along seat second side 514A are semicircular and laterally expose at least a portion of instruments 108B, 108D, respectively. Recessed portion 702C, however, is disposed along a base of a seat center exposing notch 704. As shown in FIG. 7A, notch 704 provides a matable groove which, when combined with a portion of second clamp member 412A, may be used to capture an instrument 108 (i.e., when second clamp member 412A is moved toward seat second side 514A). As discussed above, movement of actuator 510A in first direction 520 moves seat first side 512A toward first clamp member 414A and moves second clamp member 412A toward seat second side 514A. The moving of seat first side 512A and second clamp member 412A combine with recessed portions 702A, 702B, 702C, 702D, 702E to create a plurality of retainment holders for instruments 108A, 108B, 108C, 108D, 108E. Notably, the present assemblies and methods are not limited to five recessed portions as shown in FIGS. 7A-7D. In other examples, more or less than five recessed portions may be present. Further, other seat 410A configurations are also possible. As one example, seat 410A configuration may be similar to that found in FIG. 10B.

Figure 8A:
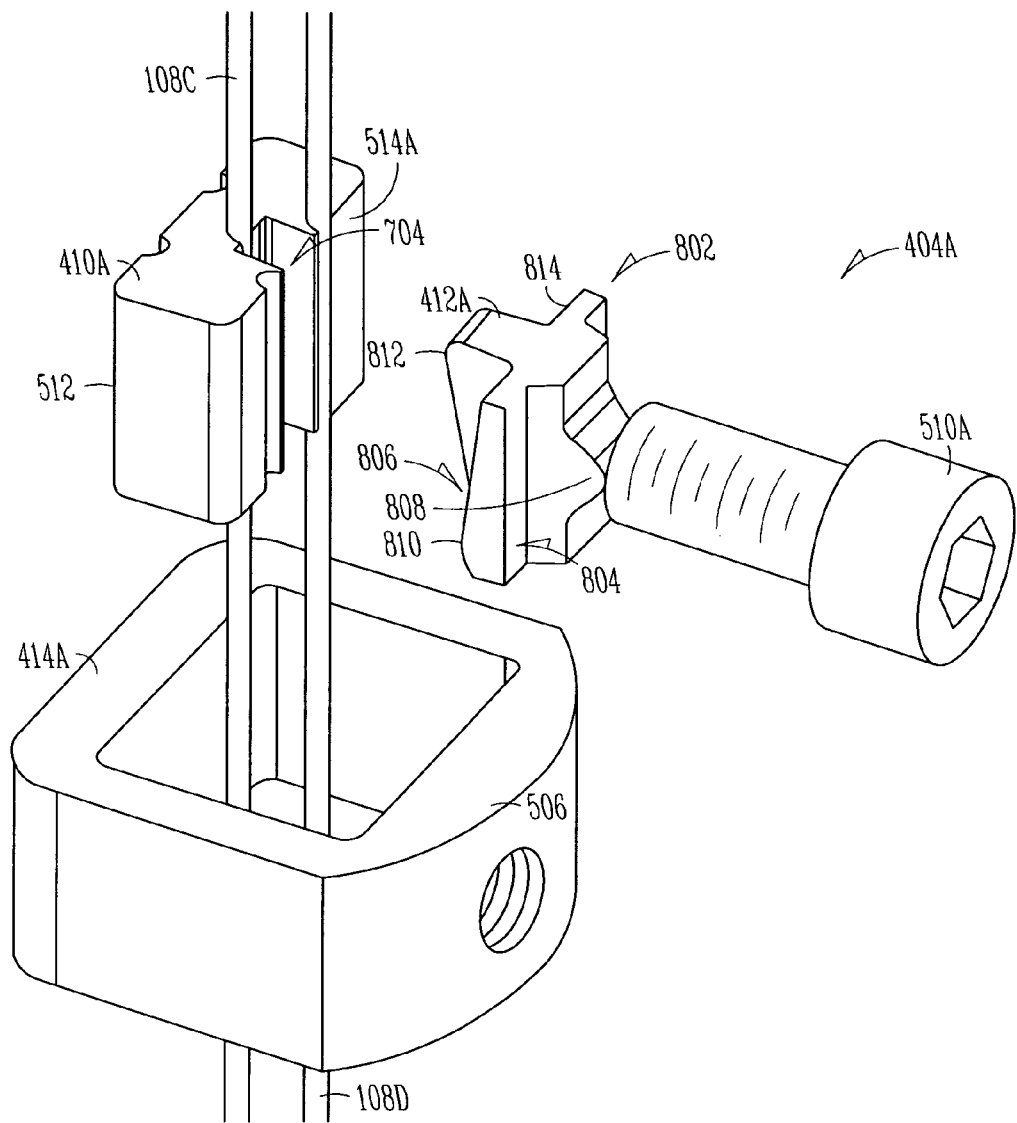
FIG. 8A is an exploded isometric view illustrating a retaining assembly and a plurality of instruments, as constructed in accordance with at least one embodiment.

FIG. 8A illustrates an exploded view of a retainment portion 404A of a retaining assembly 104A (FIG. 4A). As shown, second clamp member 412A may include a rocker 802. Rocker 802 is captured within a space defined by a seat 410A, an arm member 506, and an actuator 510A. Rocker 802, being part of second clamp member 412A, is movable toward or away from seat 410A through movement of actuator 510A as discussed above. In this example, rocker 802 includes a rocker first side 804 and an opposing rocker second side 806. Rocker first side 804 faces actuator 510A, while rocker second side 806 faces seat 410A. In one example, a rocking stud 808 extends from rocker first side 804. Rocking stud 808 is substantially adjacent an end of actuator 510. When rocker 802 is engaged by actuator 510A (e.g., by clockwise rotation of actuator 510A), rocking stud 808 is contacted by the end of actuator 510A.

Rocker second side 806 includes at least a first contact portion 810 and a second contact portion 812. In this example, rocker second side 806 includes first, second, and third contact portions 810, 812, 814, respectively. In varying examples, seat 410A and second clamp member 412A are configured to float in a space defined by arm member 506 and first clamp member 414A. The floating nature of seat 410A and second clamp member 412A combined with features of rocker 802 (e.g., opposing inclined surfaces of first, second, and third contact portions 810, 812, 814, respectively, and rocking stud 808) allows seat 410A to pivot in two-dimensions and allows second clamp member 412A to pivot in three-dimensions thereby reliably retaining (i.e., capturing) any number of instruments 108 regardless of a quantity, size, or position of such instruments.

Figure 8B:
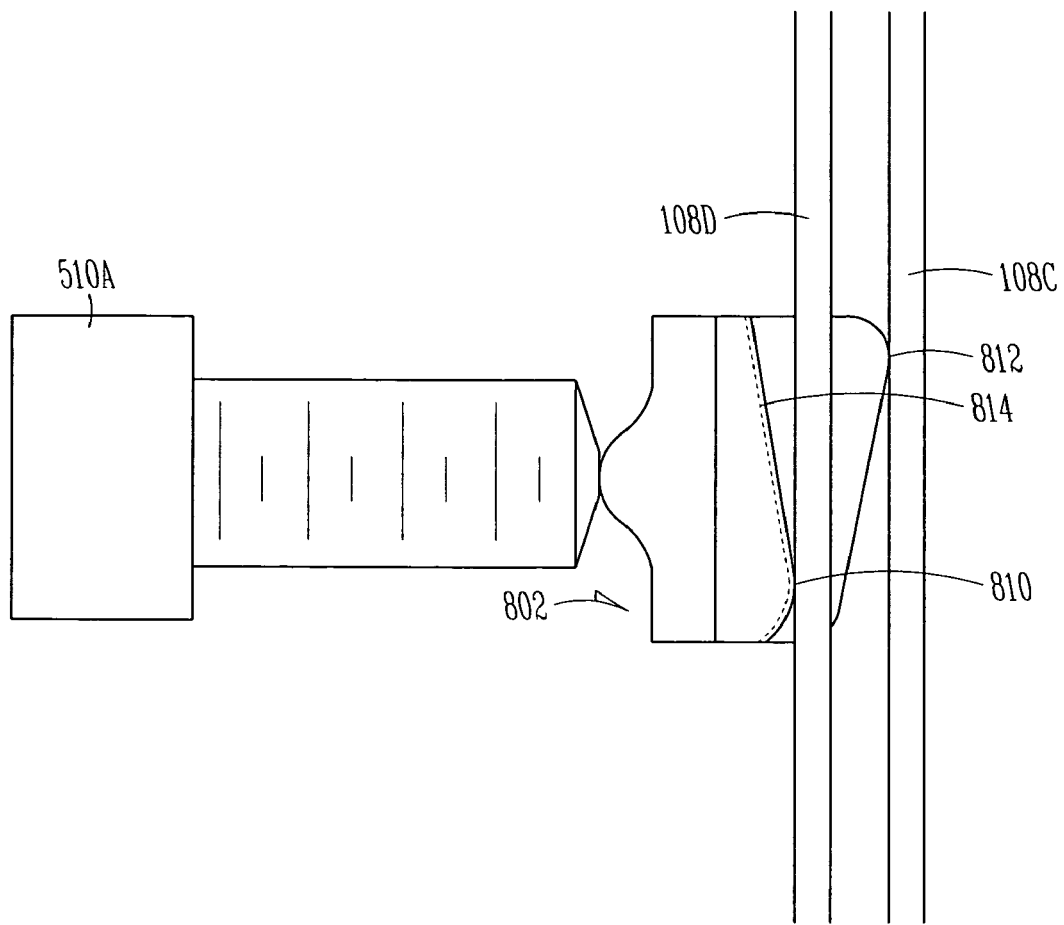
FIG. 8B is a side view illustrating portions of a retaining assembly and a plurality of instruments, as constructed in accordance with at least one embodiment.

FIG. 8B illustrates a side view of rocker 802, actuator 510A and one or more instruments 108C, 108D. As shown, first contact portion 810 and second contact portion 812 of rocker 802 engage instruments 108D and 108C, respectively. In one example, second contact portion 812 engages instrument 108C which causes first contact portion 810 to pivot about second contact 812 into engagement with instrument 108D. Advantageously, such an arrangement allows a plurality of instruments 108 to be retained by a single actuation means (e.g., actuator 510A).

Referring again to FIG. 5, which illustrates five instruments 108A, 108B, 108C, 108D, 108E retained by retainment portion 404A of retaining assembly 104A (FIG. 4A). The five instruments 108A, 108B, 108C, 108D, 108E shown in FIG. 5 may be of varying diameters, as the retainment portion 404A is configured to retain instruments of varying diameters that otherwise fit through track portion 408A (FIG. 4A). In one example, instruments 108A, 108B, 108C, 108D, 108E are fed (e.g., by hand) through tracks 302A, 304A (FIG. 4A) and the corresponding recessed portions 702A, 702B, 702C, 702D, 702E (FIG. 7B) of seat 410A. After insertion of instruments 108A, 108B, 108C, 108D, 108E, actuator 510A may be rotated thereby causing a distal end thereof to contact a rocker first side 804 (FIG. 8A). Once engaged to rocker 802, actuator 510A and rocker 802 collectively move toward seat 410A. In one example, a first contact portion 810 of rocker 802 engages instruments 108B, 108D disposed within recessed portions 702B, 702D, respectively, and retains such instruments against seat second side 514A. Further movement of actuator 510A in direction 520 causes rocker 802, specifically second contact portion 812, to pivot about first contact 810 thereby engaging instrument 108C in recessed portion 702C.

In the retainment portion 404A configuration shown in FIG. 5, movement of actuator 510A in direction 520 causes seat first side 512A to move toward first clamp member 414A in addition to causing rocker 802 to be pushed toward seat second side 514A. The moving of seat first side 512A engages instruments 108A, 108E in recessed portions 702A, 702E, respectively, and retains such instruments against seat first side 512A.

Figure 6:
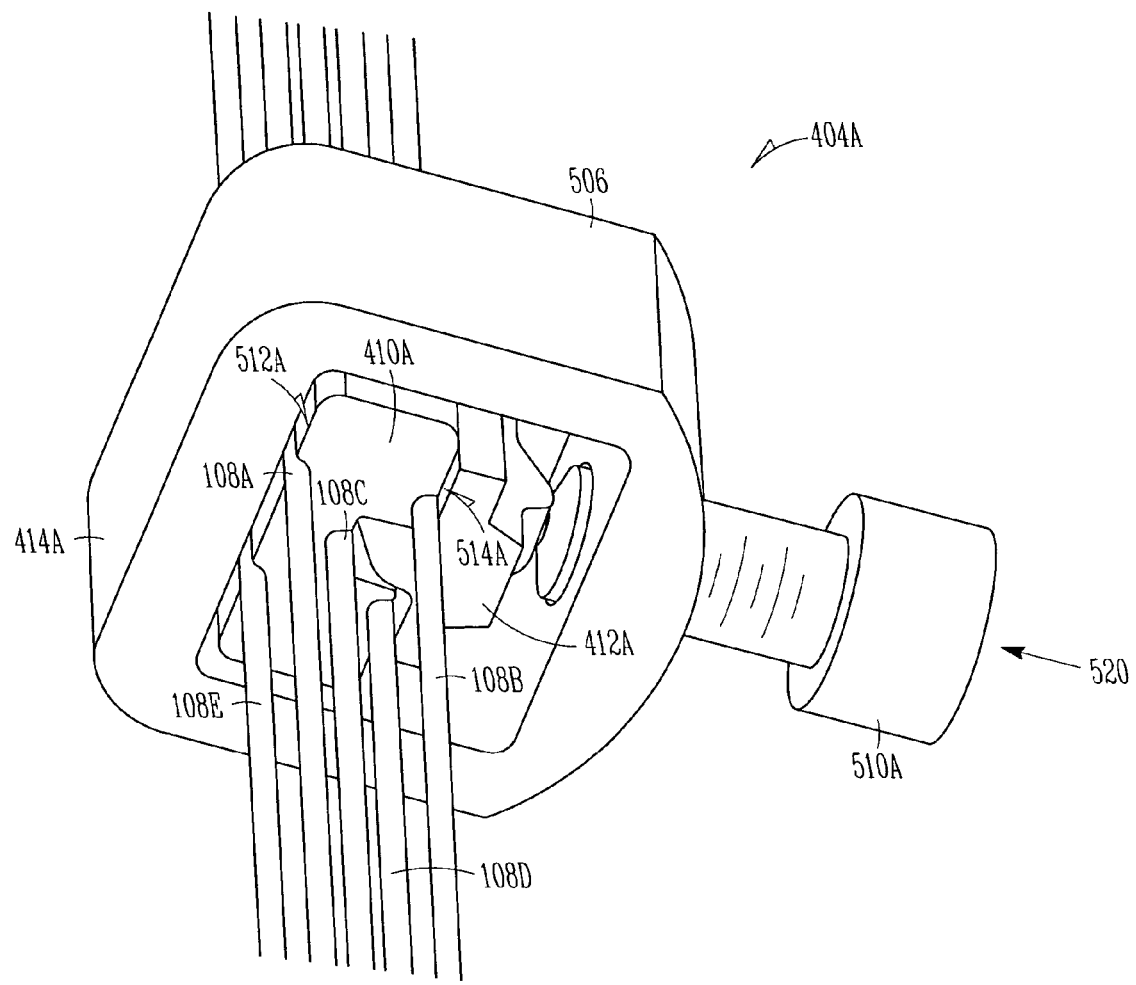
FIG. 6 is an isometric view from a bottom direction illustrating a retaining assembly and a plurality of instruments, as constructed in accordance with at least one embodiment.

With the movement of actuator 510A in direction 520, in this example, five separate instruments 108A, 108B, 108C, 108D, 108E all of identical size are retained by retainment portion 404A by way of a single actuation means. In another example, retainment portion 404A includes additional recessed portions to retain additional instruments. In still another example, less than five instruments are retained in retainment portion 404A. In yet another example, where arm member 506 and first clamp member 414A are integral and form a collar that substantially surrounds seat 410A, seat first side 512A is moved toward a portion of the collar when actuator 510A is advanced in direction 520 and rocker 802 (or other second clamp member 412A) is engaged with seat second side 514A. FIG. 6 illustrates an isometric bottom view of retainment portion 404A shown in FIG. 5.

Figure 7C:
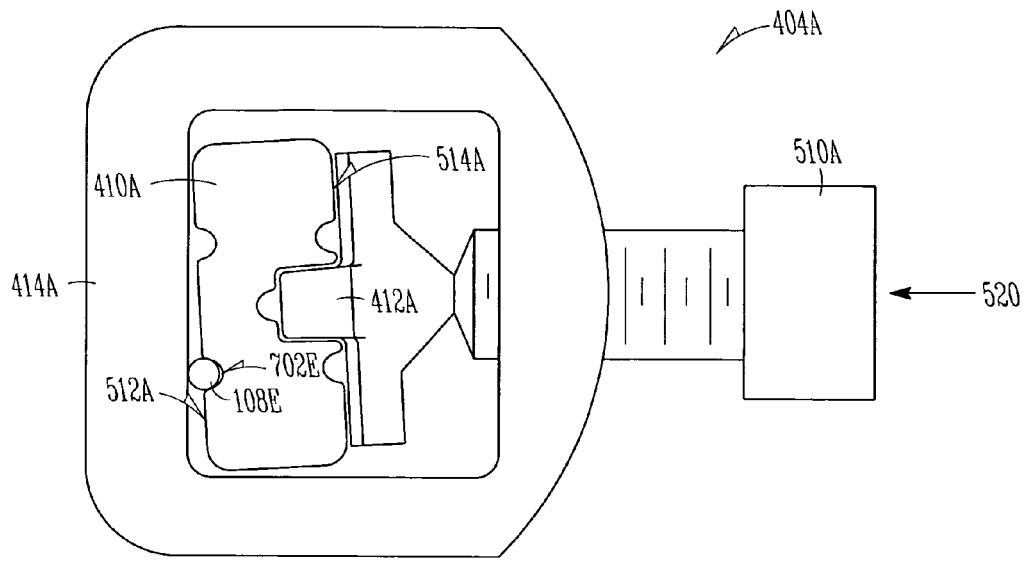
FIG. 7C is a top view illustrating a retaining assembly and an instrument, as constructed in accordance with at least one embodiment.
Figure 7D:
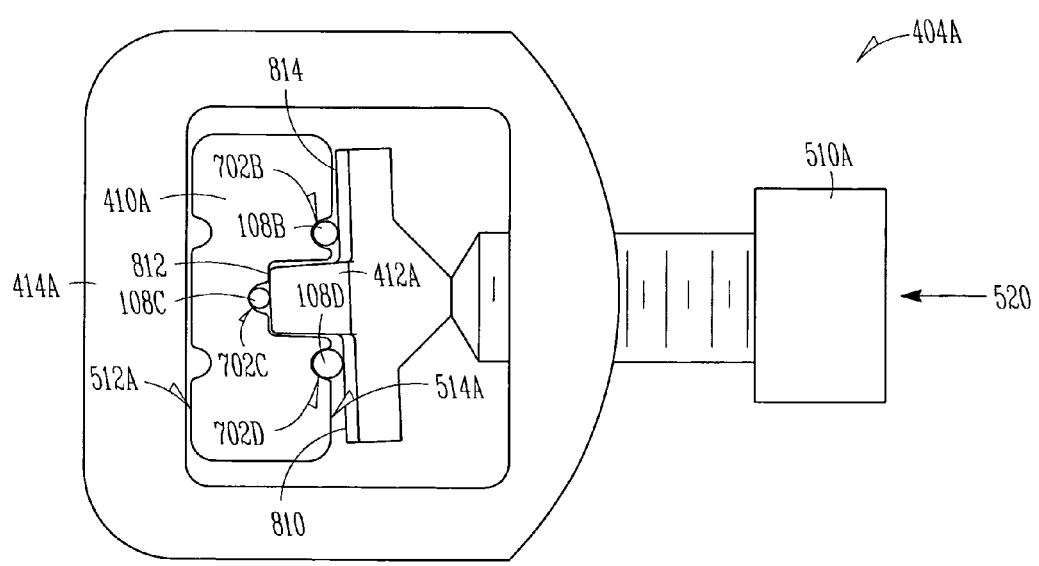
FIG. 7D is a top view illustrating a retaining assembly and a plurality of instruments, as constructed in accordance with at least one embodiment.

Referring to FIGS. 7C and 7D, which illustrate a top view of a seat 410A of a retainment portion 404A. As discussed above, seat first side 512A is configured to pivot in two-dimensions, while second clamp member 412A is configured to pivot in three-dimensions. As a result of such configuration, any number of instruments 108 may be retained regardless of a quantity, size, or position of such instruments. As shown in FIG. 7C, a single instrument 108E is retained between first clamp member 414A and seat first side 512A. In this example, as actuator 510A is moved in first direction 520, seat first side 512A, specifically seat recessed portion 702E, eventually contacts a portion of instrument 108E thereby causing seat 410A to pivot about such contact point until an opposite end of seat first side 512A contacts first clamp member 414A.

Similarly, as shown in FIG. 7D, three instruments 108D, 108C, 108B of varying size (i.e., 108D>108B>108C) are retained between second clamp member 412A and seat second side 514A. In this example, as actuator 510A is moved in first direction 520, seat first side mates up against first clamp member 414A as a result of no instruments being present between seat first side 512A and first clamp member 414A. As actuator 510A is further moved in first direction 520, a first contact portion 810 contacts a portion of large-sized instrument 108D thereby causing second clamp member 412A to pivot about such contact point until third contact portion 814 contacts a portion of medium-sized instrument 108B. Due to first and third contact portions 810, 814 contacting instruments 108D and 108B, respectively, second clamp member 412A is confined in two-dimensions. However, the present assemblies are configured to advantageously allow second clamp member 412A to pivot in three-dimensions. As a result, further movement of actuator 510A in first direction 520 causes a leading edge of second contact portion 812 to pivot against small-sized instrument 108C. It will be appreciated by those skilled in the art that the present assemblies and methods may be utilized with any (quantity, size, or position) combination of instruments, as such, FIGS. 7C and 7D are intended only to be illustrative, and not restrictive.

Figure 9A:
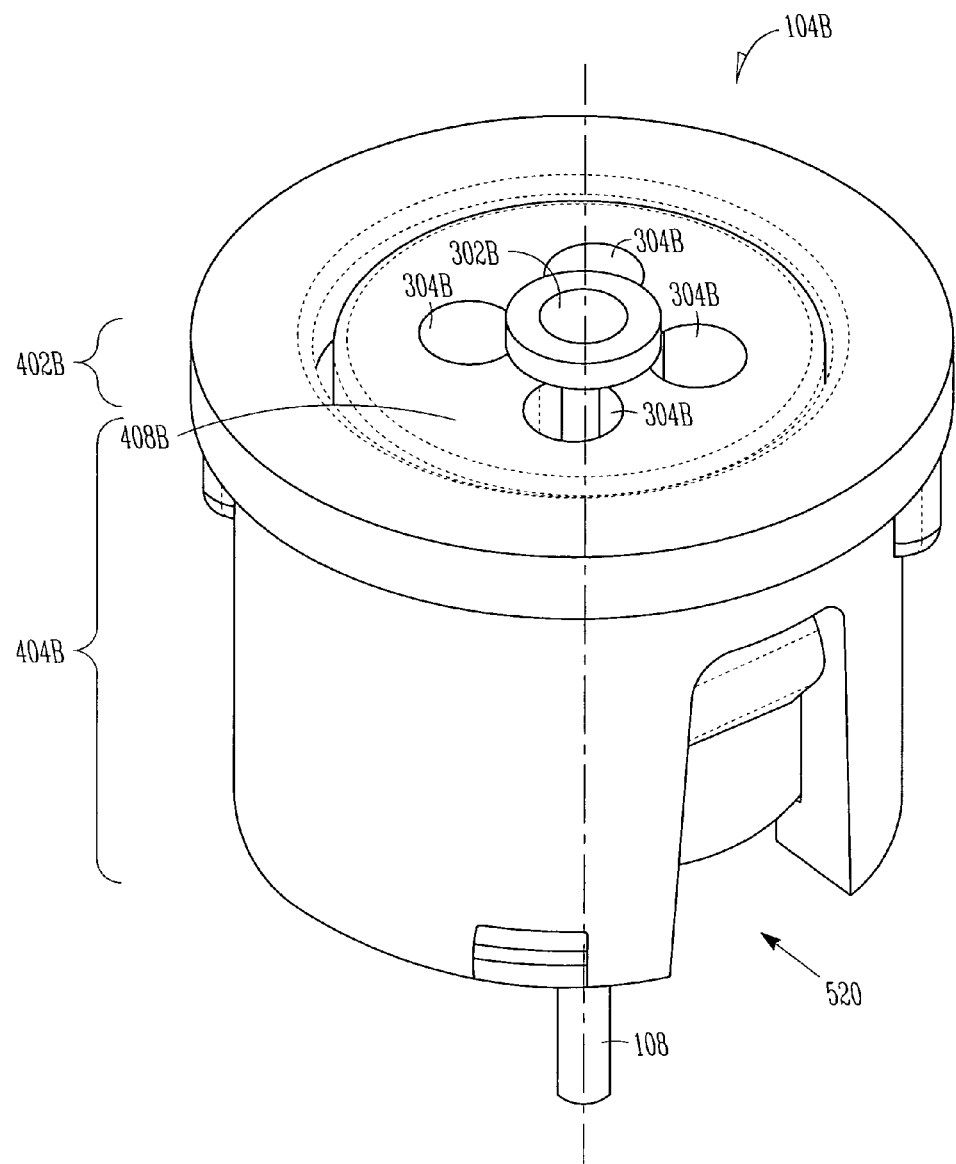
FIG. 9A is an isometric view illustrating portions of a retaining assembly and a trajectory guide tube, as constructed in accordance with at least one embodiment.

FIG. 9A illustrates portions of another retaining assembly 104B couplable with a drive and trajectory guide assembly 100 (FIG. 1). As shown, retaining assembly 104B includes a cap portion 402B and a retainment portion 404B. In varying examples, retaining assembly 104B includes a track portion 408B that provides one or more tracks (e.g., 302B, 304B) into which one or more instruments 108 (FIG. 4A), such as trajectory guide tubes, may be inserted and thereafter retained (by retainment portion 404B). In this example, retainment portion 404B includes, among other things, a seat 410B (FIG. 9B), a first clamp member 414B (FIG. 9B), a second clamp member 412B (FIG. 9B), a collar 902 (FIG. 9B), and an actuator 510B (FIG. 10A).

Figure 9B:
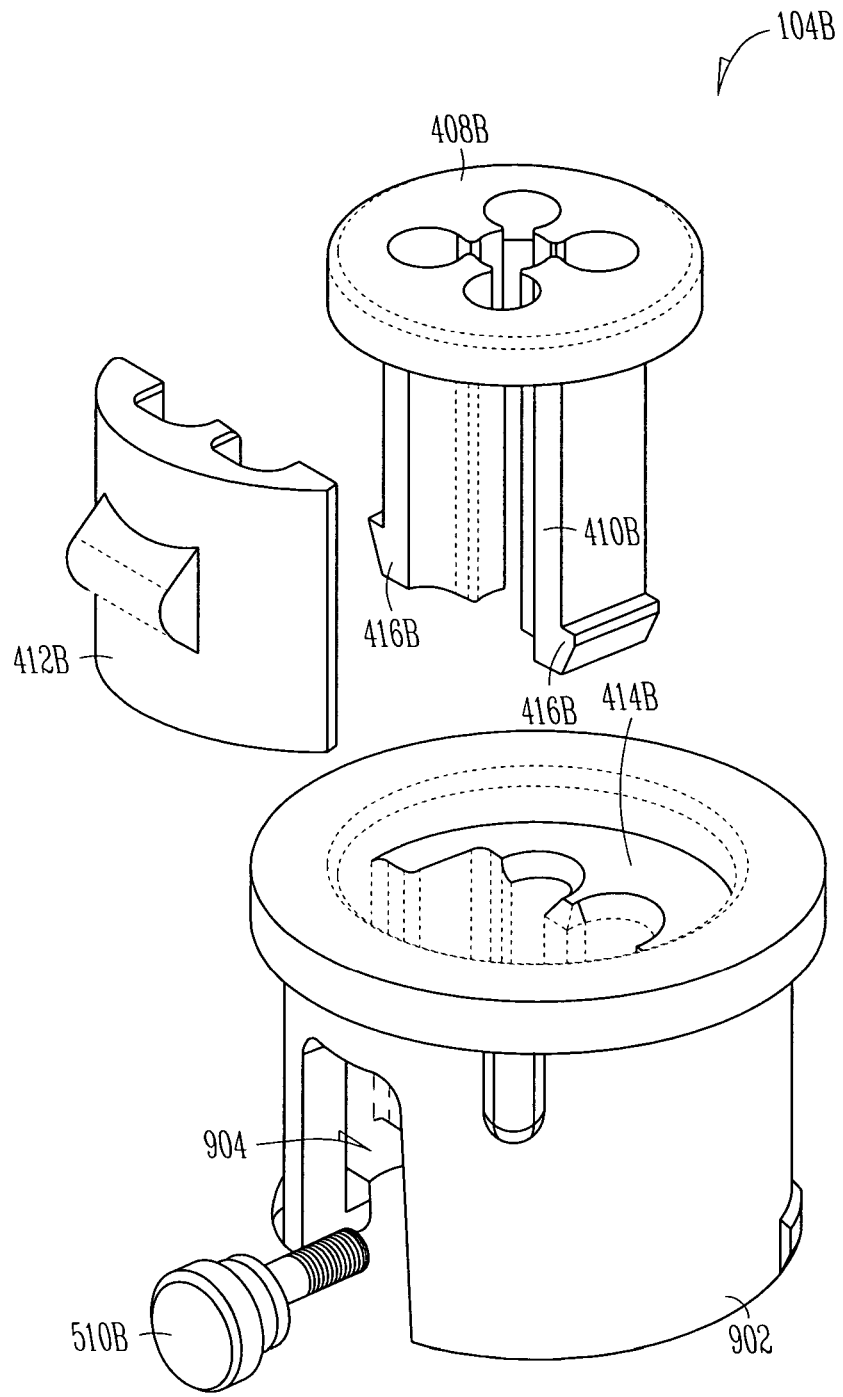
FIG. 9B is an exploded isometric view illustrating portions of a retaining assembly, as constructed in accordance with at least one embodiment.

FIG. 9B illustrates an exploded view of portions of retaining assembly 104B of FIG. 9A. As shown in FIG. 9B, track portion 408B is coupled to seat 410B (of retainment portion 404B). Positioned to the left of seat 410B, is a second clamp member 412B (of retainment portion 404B) configured to be brought into engagement with seat 410B. In this example, seat 410B includes two tabs 416B positioned opposite one another. Tabs 416B may provide floating coupling of seat 410B within collar 902.

Figure 10A:
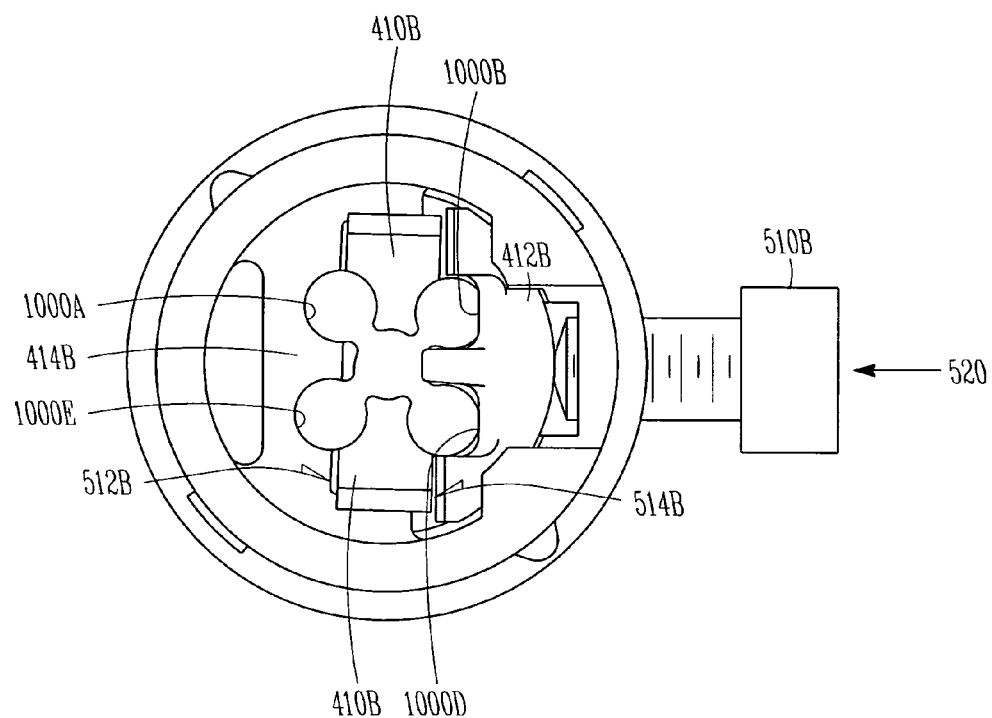
FIG. 10A is a top view illustrating a retaining assembly, as constructed in accordance with at least one embodiment.
Figure 10B:
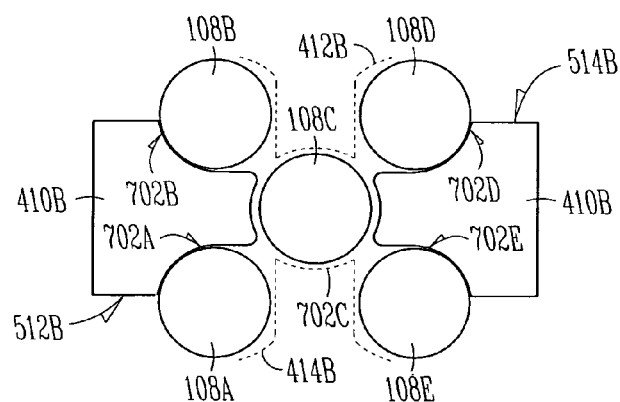
FIG. 10B is a top view illustrating a seat member of a retaining assembly and a plurality of instruments, as constructed in accordance with at least one embodiment.

Referring now to FIGS. 10A and 10B, which illustrate, among other things, a top view of a seat 410B of retainment portion 404B shown in FIG. 9A. Seat 410B includes a seat first side 512B and an oppositely positioned seat second side 514B. As shown, both seat first side 512B and seat second side 514B include one or more recessed portions. Specifically, seat first side 512B and seat second side 514B both include two recessed portions 702A, 702E and 702B, 702D, respectively. In addition, first clamp member 414B and second clamp member 412B combine to form recessed portion 702C configured to capture instrument 108C when actuator 510B is advanced in first direction 520 (see FIG. 10B, specifically the recessed portion created by a portion of first clamp member 414B and second clamp member 412B— shown by phantom lines). Each recessed portion 702A, 702B, 702D, 702E is configured to provide a groove capable of receiving an instrument 108A, 108B, 108D, 108E, respectively. In this example, first clamp member 414B and second clamp member 412B include one or more recessed portions as well. Specifically, first clamp member 414B includes recessed portions 1000A, 1000E, while second clamp member 412B includes recessed portions 1000B, 1000D.

In the retainment portion 404B configuration of FIGS. 9A, 9B, 10A, 10B, movement of actuator 510B (through collar void 904) in direction 520 moves seat first side 512B toward first clamp member 414B and collar 902 and moves second clamp member 412B toward seat second side 514B. The moving of seat first side 512B and second clamp member 412B combine with recessed portions 702A, 702B, 702D, 702E and 1000A, 1000B, 1000D, 1000E to create a plurality of retainment holders for instruments 108A, 108B, 108D, 108E. In addition, as discussed above, movement of actuator 510B in direction 520 creates a retainment holder for instrument 108C via cooperative involvement of first and second clamp members 414B, 412B, respectively.

Figure 11:
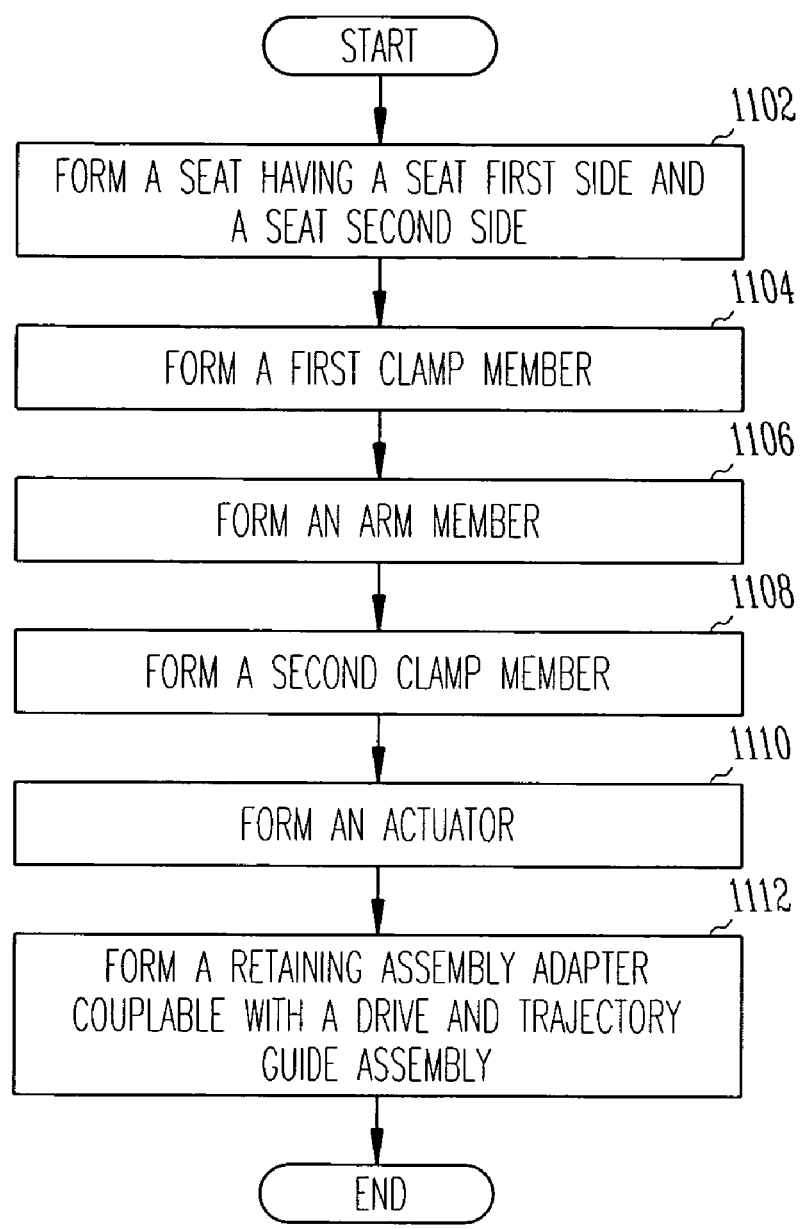
FIG. 11 is a flow diagram illustrating a method of manufacturing a retaining assembly, as constructed in accordance with at least one embodiment.

FIG. 11 is a flow diagram illustrating a method 1100 for manufacturing an assembly for retaining a plurality surgical instruments by way of a single actuation means. At 1102, a seat having a seat first side and a seat second side and including one or more recessed portions is formed. At 1104, a first clamp member having a first side surface is formed. The first clamp member is disposed adjacent to the seat first side such that the first side surface of the first clamp may be used, in part, to retain one or more instruments. At 1106, an arm member extending from the first clamp member is formed. In varying examples, the arm member extends substantially toward the seat second side. In one example, although not necessary, the arm member is integral with the first clamp member and extends completely around the seat thereby creating a collar. At 1108, a second clamp member positionable between the arm member and the seat second side is formed. The second clamp member includes a second side surface against which one or more instruments may be retained. At 1110, an actuator engagable with an actuator receiving lumen is formed. In one example, the actuator includes threads that mate with internal threads of the actuator receiving lumen. At 1112, an adapter for coupling the retaining assembly to a drive and trajectory guide assembly is formed.

Several options for manufacturing the retaining assembly are as follows. In one example, forming the second clamp member includes forming a rocker, the rocker including a rocking stud on a rocker first side and at least first and second contact portions on a rocker second side. In another example, forming the seat further comprises forming a seat center exposing notch on one or both of the seat first side or the seat second side. In one such example, at least one recessed portion is positioned at the base of the notch.

Figure 12:
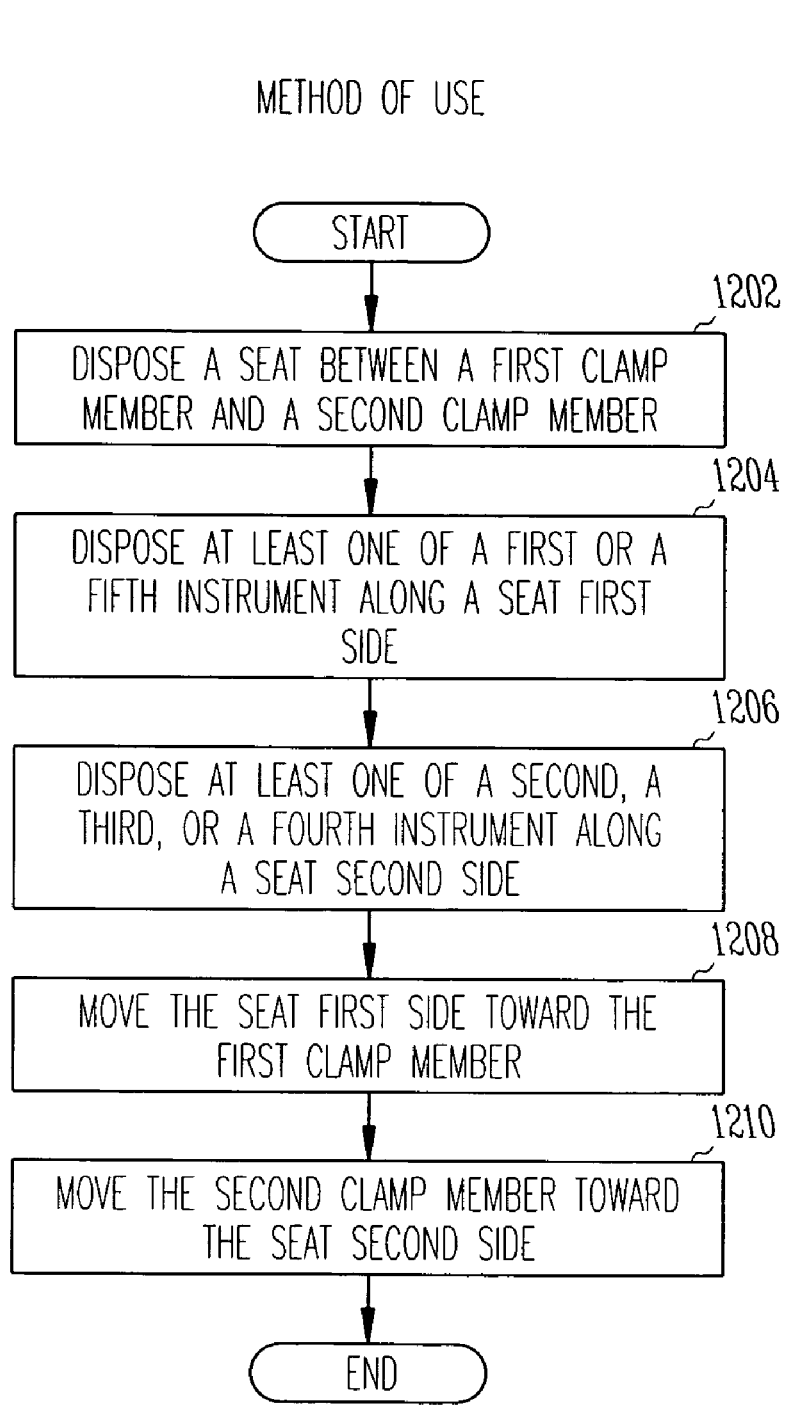
FIG. 12 is a flow diagram illustrating a method of using a retaining assembly, as constructed in accordance with at least one embodiment.

FIG. 12 is a flow diagram illustrating a method 1200 for using an assembly for retaining a plurality of surgical instruments by way of a single actuation means. At 1202, a seat is disposed between a first clamp member and a second clamp member. At 1204, at least one of a first or a fifth instrument are disposed along a seat first side. Similarly, at 1206, at least one of a second, a third, or a fourth instrument are disposed along a seat second side. At 1208 and 1210, the seat first side is moved toward the first clamp member and the second clamp member is moved toward the seat second side. In varying examples, such moving occurs as a result of actuator movement in a first direction.

Several options for using the retaining assembly are as follows. In one example, disposing the instruments includes utilizing one or more seat recessed portions. In another example, movement of an actuator is caused by rotating a threaded actuator engaged within a threaded actuator receiving lumen. In yet another example, moving the seat first side includes pivoting the seat about at least the first instrument, while moving the second clamp member includes pivoting the second clamp member about at least the second instrument or seat second side.

CONCLUSION

The retaining assembly embodiments discussed in this patent document may be used with a variety of assemblies for introducing and guiding one or more instruments into a target location with a subject's body, including the assemblies discussed above. In addition, the retaining assemblies and methods therefor discussed herein are not limited to use with assemblies used for introducing and guiding instruments.

Advantageously, the present assemblies and methods include many desirable characteristics not found in the prior art including employment of a plurality of retainment holders, such as five retainment holders, driven by one actuation input means. In addition, the present assemblies are inexpensive to manufacture, yet provide a user (e.g., a surgeon) with a good "feel" of the actual retainment force being applied to each instrument. Several other advantages are also made possible by the present assemblies and include the ability to be used with instruments of varying size and the ability to retain the instrument via a relative small actuation force.

It is to be understood that the above description is intended to be illustrative, and not restrictive. For example, the above detailed description may be used in combination with each other. Many other embodiments will be apparent to those of skill in the art upon reading and understanding the above description. The scope of the invention should, therefore, be determined with reference to the appended claims, along with the full scope of legal equivalents to which such claims are entitled. In the appended claims, the term "including" is used as the plain-English equivalent of the term "comprising." Also, in the following claims, the terms "including" and "comprising" are open-ended, that is, a system, assembly, device, or method that includes elements in addition to those listed after such a term in a claim are still deemed to fall within the scope of that claim.

The Abstract of the disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate embodiment.

What is claimed is:

1. An assembly for retaining a plurality of surgical instruments, the assembly comprising:
   a seat including a seat first side and a seat second side, the seat first side positioned opposite the seat second side;
   a first clamp member positioned adjacent the seat first side;
   an arm member that is disposed at a fixed distance away from the first clamp member;
   a second clamp member positioned adjacent the seat second side; and
   an actuator located adjacent the seat second side and operably coupled to the arm member, wherein the actuator includes a threaded screw and wherein the arm member includes an actuator receiving lumen having one or more threads matable with the threaded screw;
   wherein the seat and the second clamp member are moveably disposed between the arm member and the first clamp member, and
   wherein movement of the actuator in a first direction moves the seat first side toward the first clamp member and moves the second clamp member toward the seat second side.

2. The assembly as recited in claim 1, wherein the arm member extends from the first clamp member substantially toward the seat second side.

3. The assembly as recited in claim 1, wherein a retaining orientation of the seat or the second clamp member is dependent on a position, a size, or a quantity of the surgical instruments to be retained.

4. The assembly as recited in claim 1, wherein one or both of the seat first side or the seat second side include one or more recessed portions, each recessed portion comprising a part of a retainment holder when the actuator is substantially moved in the first direction.

5. The assembly as recited in claim 1, wherein the second clamp member comprises a rocker configured to pivot about one or more surgical instruments to be retained or the seat second side when engaged by movement of the actuator in the first direction.

6. The assembly as recited in claim 5, wherein the rocker comprises a rocker first side facing the actuator, the rocker first side including a rocking stud; and a rocker second side facing the seat second side, the rocker second side including at least first and second contact portions; and wherein the rocking stud and the first and second contact portions are configured to allow the rocker to pivot in three dimensions.

7. A drive and trajectory guide assembly including the assembly of claim 1 coupled thereto.

8. The assembly as recited in claim 7, wherein an actuator receiving lumen is formed in a second stage of the drive and trajectory guide assembly.

9. An assembly for retaining a plurality of surgical instruments, the assembly comprising:

a floating seat including a seat first side and a seat second side, the seat first side positioned opposite the seat second side;

a first clamp member positioned adjacent the seat first side and a floating second clamp member positioned adjacent the seat second side;

a collar substantially surrounding a portion of the floating seat and the floating second clamp member;

an actuator disposed near the second clamp member; and wherein movement of the actuator in a first direction advances the first clamp member, the floating seat, and the floating second clamp member toward one another.

10. The assembly as recited in claim 9, wherein the collar comprises an arm member extending from a first clamp member first end to a first clamp member second end.

11. The assembly as recited in claim 9, wherein an actuator receiving lumen engagable with the actuator is positioned in the collar.

12. The assembly as recited in claim 9, wherein the floating second clamp member comprises a rocker configured to pivot in three dimensions about one or more surgical instruments to be retained or the seat second side.

13. The assembly as recited in claim 12, wherein the rocker comprises a rocker first side oriented adjacent an actuator distal end, the rocker first side including a rocking stud; and a rocker second side oriented adjacent the seat second side, the rocker second side including at least first and second contact portions; and wherein the rocking stud is configured to transfer movement of the actuator in the first direction to the at least first and second contact portions of the rocker second side.

14. The assembly as recited in claim 9, wherein one or both of the seat first side or the seat second side comprise one or more recessed portions, each recessed portion comprising a part of a retainment holder when the actuator is substantially moved in the first direction.

15. A drive and trajectory guide assembly including the assembly of claim 9 coupled thereto.

16. The assembly as recited in claim 15, wherein an actuator receiving lumen is formed in a second stage of the drive and trajectory guide assembly.

17. A retainment assembly comprising:

a collar including an inner surface;

a floating seat at least partially within the collar, the seat including at least two recessed portions;

a floating clamp member positioned between the collar and the floating seat, the floating clamp member including a clamp member first side adjacent the inner surface of the collar and a clamp member second side adjacent the floating seat; and an actuator received in, and engageable with, an actuator receiving lumen.

18. The assembly as recited in claim 17, wherein movement of the actuator in a first direction advances both the floating seat and the floating clamp member toward a portion of the inner surface of the collar.

19. The assembly as recited in claim 17, wherein the floating clamp member comprises a rocker engagable with one or more recessed portions of the seat to form one or more retainment holders when the actuator is substantially moved in a first direction.

20. The assembly as recited in claim 17, wherein the rocker comprises a rocking stud on a rocker first side; and at least first and second contact portions on a rocker second side; and wherein the rocking stud and the first and second contact portions are configured to pivot the rocker in three dimensions about one or more instruments to be retained or a portion of the floating seat.

21. A drive and trajectory guide assembly including the assembly of claim 17 coupled thereto.

22. The assembly as recited in claim 21, wherein the actuator receiving lumen is formed in a first stage of the drive and trajectory guide assembly.

23. A method of using an assembly for retaining a plurality of surgical instruments, the method comprising:

providing a floating seat including a seat first side and a seat second side, the seat first side positioned opposite the seat second side;

providing a first clamp member positioned adjacent the seat first side and a floating second clamp member positioned adjacent the seat second side;

providing a collar substantially surrounding a portion of the floating seat and the floating second clamp member;

providing an actuator disposed near the second clamp member;

disposing at least a first instrument along the seat first side;

disposing at least a second instrument along the seat second side;

moving the actuator in a first direction to advance the first clamp member, the floating seat, and the floating second clamp member toward one another, to move the seat first side toward the first clamp member to retain the first instrument against the seat first side, and to move the second clamp member toward the seat second side to retain the second instrument against the seat second side.

24. The method as recited in claim 23, wherein disposing the second instrument along the seat second side includes disposing the second instrument in a position opposite the a position of the first instrument.

25. The method as recited in claim 23, wherein disposing the first instrument and the second instrument includes disposing the first instrument and the second instrument along one or more seat recessed portions.

26. The method as recited in claim 23, claim wherein moving the actuator includes rotating a screw.

27. The method as recited in claim 23, further comprising disposing at least a third instrument along a recessed portion of the seat second side.

28. The method as recited in claim 27, further comprising disposing a fourth instrument along another recessed portion of the seat second side, and disposing a fifth instrument along a recessed portion of the seat first side; and wherein moving the actuator includes retaining the first and fifth instruments against the seat first side, and wherein moving the actuator includes retaining the second, third, and fourth instruments against the seat second side.

29. The method as recited in claim 23, wherein moving the actuator includes pivoting the seat about at least the first instrument.

30. The method as recited in claim 23, wherein moving the actuator includes pivoting the second clamp member about at least the second instrument or seat second side.

31. An assembly for retaining a plurality of surgical instruments, the assembly comprising:
   a collar having a first clamp member, the collar being ring-shaped so as to define an opening;
   a seat moveably disposed in the opening of the collar, the seat including a seat first side and a seat second side, the seat first side positioned opposite the seat second side, the seat first side positioned adjacent the first clamp member, the seat first side and the seat second side each including a recessed portion able to receive at least one of the plurality of surgical instruments;
   a second clamp member moveably disposed in the opening of the collar, the second clamp member positioned adjacent the seat second side, the second clamp member including a rocker that pivots the second clamp member relative to the seat; and
   a threaded screw that is threadably received within a threaded lumen in the collar, wherein movement of the actuator in a first direction moves the seat first side toward the first clamp member, moves the second clamp member toward the seat second side, and pivots the second clamp member relative to the seat to retain the plurality of instruments in the recessed portions.

32. The assembly as recited in claim 31, wherein the rocker includes a rocker first side facing the threaded screw, the rocker first side including a rocking stud, the rocker also including a rocker second side facing the seat second side, the rocker second side including at least first and second contact portions, and wherein the rocking stud and the first and second contact portions are configured to allow the rocker to pivot in three dimensions.

33. The assembly of claim 2, wherein the arm member extends from a first end of the first clamp member to a second end of the first clamp member.

\* \* \* \* \*